United States Patent
Purohit et al.

(10) Patent No.: US 12,239,300 B2
(45) Date of Patent: Mar. 4, 2025

(54) BIOPSY FORCEPS WITH SERRATED CUTTING JAWS

(71) Applicant: Boston Scientific Medical Device Limited, Galway (IE)

(72) Inventors: Hitendra Purohit, Vadodara (IN); Agrim Mishra, New Delhi (IN); Rohit Rohilla, Haryana (IN); Abhishek Basu, Haryana (IN)

(73) Assignee: Boston Scientific Medical Device Limited, Galway (IE)

( * ) Notice: Subject to any disclaimer, the term of this patent is extended or adjusted under 35 U.S.C. 154(b) by 1385 days.

(21) Appl. No.: 16/355,914

(22) Filed: Mar. 18, 2019

(65) Prior Publication Data

US 2019/0282220 A1    Sep. 19, 2019

Related U.S. Application Data

(60) Provisional application No. 62/644,892, filed on Mar. 19, 2018.

(51) Int. Cl.
*A61B 10/06* (2006.01)
*A61B 10/02* (2006.01)
(Continued)

(52) U.S. Cl.
CPC .............. *A61B 10/06* (2013.01); *A61B 10/04* (2013.01); *A61B 17/282* (2013.01); *A61B 17/29* (2013.01);
(Continued)

(58) Field of Classification Search
CPC ....... A61B 10/06; A61B 17/282; A61B 17/29; A61B 2017/2926; A61B 2017/2945
See application file for complete search history.

(56) References Cited

U.S. PATENT DOCUMENTS

D71,440 S    11/1926    Villaret
4,682,606 A    7/1987    De Caprio
(Continued)

FOREIGN PATENT DOCUMENTS

| EP | 2 324 773 | 5/2011 |
| JP | 2006527633 A | 12/2006 |
| WO | WO 98/40015 | 9/1998 |

OTHER PUBLICATIONS

Engineering ToolBox, (2003). Young's Modulus—Tensile and Yield Strength for common Materials. Version Sep. 18, 2015. [online] Available at: https://www.engineeringtoolbox.com/young-modulus-d_417.html. Accessed via Wayback Machine Feb. 16, 2021. (Year: 2015).

(Continued)

*Primary Examiner* — Rene T Towa
*Assistant Examiner* — Huong Q Nguyen
(74) *Attorney, Agent, or Firm* — Bookoff McAndrews, PLLC

(57) ABSTRACT

A biopsy forceps includes an end effector with opposing first and second jaws coupled together and configured to move from an open configuration to a closed configuration. Each of the first jaw and the second jaw includes a plurality of teeth having a base. The bases of two adjacent teeth of the first jaw are spaced apart to form a first gap, and the bases of two adjacent teeth on the second jaw are spaced apart to form a second gap. The end effector in the closed configuration may define one or more windows between edges of the first and the second jaws. And, at least one of these windows may include at least a portion of one or both of the first and second gaps.

14 Claims, 11 Drawing Sheets

(51) Int. Cl.
*A61B 10/04* (2006.01)
*A61B 17/28* (2006.01)
*A61B 17/29* (2006.01)
*A61B 17/295* (2006.01)

(52) U.S. Cl.
CPC .... *A61B 17/295* (2013.01); *A61B 2010/0208* (2013.01); *A61B 10/0266* (2013.01); *A61B 2017/2901* (2013.01); *A61B 2017/2926* (2013.01)

(56) References Cited

U.S. PATENT DOCUMENTS

| | | | |
|---|---|---|---|
| 5,304,203 | A | 4/1994 | El-Mallawany et al. |
| 5,553,624 | A | 9/1996 | Francese et al. |
| 5,779,646 | A | 7/1998 | Koblish et al. |
| 5,819,738 | A * | 10/1998 | Slater ............... A61B 10/06 606/205 |
| 5,906,630 | A | 5/1999 | Anderhub et al. |
| 6,036,656 | A | 3/2000 | Slater |
| 6,309,404 | B1 | 10/2001 | Krzyzanowski |
| 6,394,964 | B1 | 5/2002 | Sievert et al. |
| 6,514,269 | B2 | 2/2003 | Yamamoto |
| 8,672,859 | B2 | 3/2014 | Timberlake et al. |
| 8,740,853 | B2 | 6/2014 | Szweda et al. |
| 9,592,035 | B2 | 3/2017 | Vetter et al. |
| 9,681,857 | B2 | 6/2017 | Rothberg et al. |
| 2004/0260337 | A1 | 12/2004 | Freed |
| 2006/0184198 | A1 | 8/2006 | Bales et al. |
| 2007/0083228 | A1 * | 4/2007 | Visinoni ............ A61B 10/06 606/210 |
| 2007/0244509 | A1 | 10/2007 | Weizman et al. |
| 2009/0264795 | A1 | 10/2009 | Dunn |
| 2013/0066230 | A1 | 3/2013 | Li et al. |
| 2013/0085412 | A1 | 4/2013 | Timberlake et al. |
| 2013/0131544 | A1 | 5/2013 | Bowden et al. |
| 2015/0148803 | A1 | 5/2015 | Kaneko et al. |
| 2016/0100851 | A1 | 4/2016 | Van Andel |
| 2016/0256140 | A1 | 9/2016 | Haack et al. |
| 2016/0262735 | A1 | 9/2016 | Gundberg et al. |
| 2017/0071585 | A1 | 3/2017 | Adkisson et al. |
| 2020/0054309 | A1 | 2/2020 | Krzyzanowski |

OTHER PUBLICATIONS

Official Communication in European Patent Application No. 19717609.2, dated Aug. 30, 2022 (5 pages).

* cited by examiner

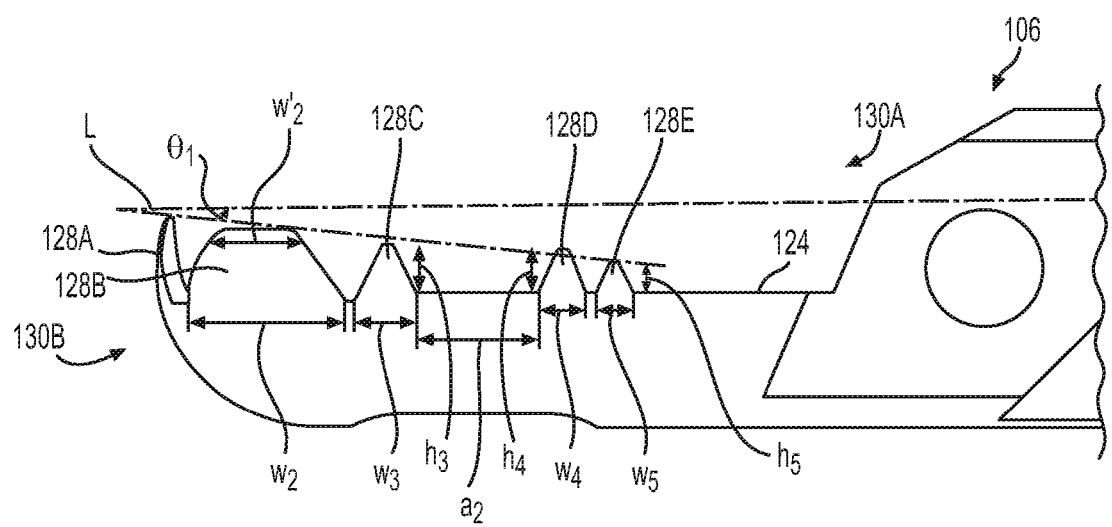
FIG. 10A
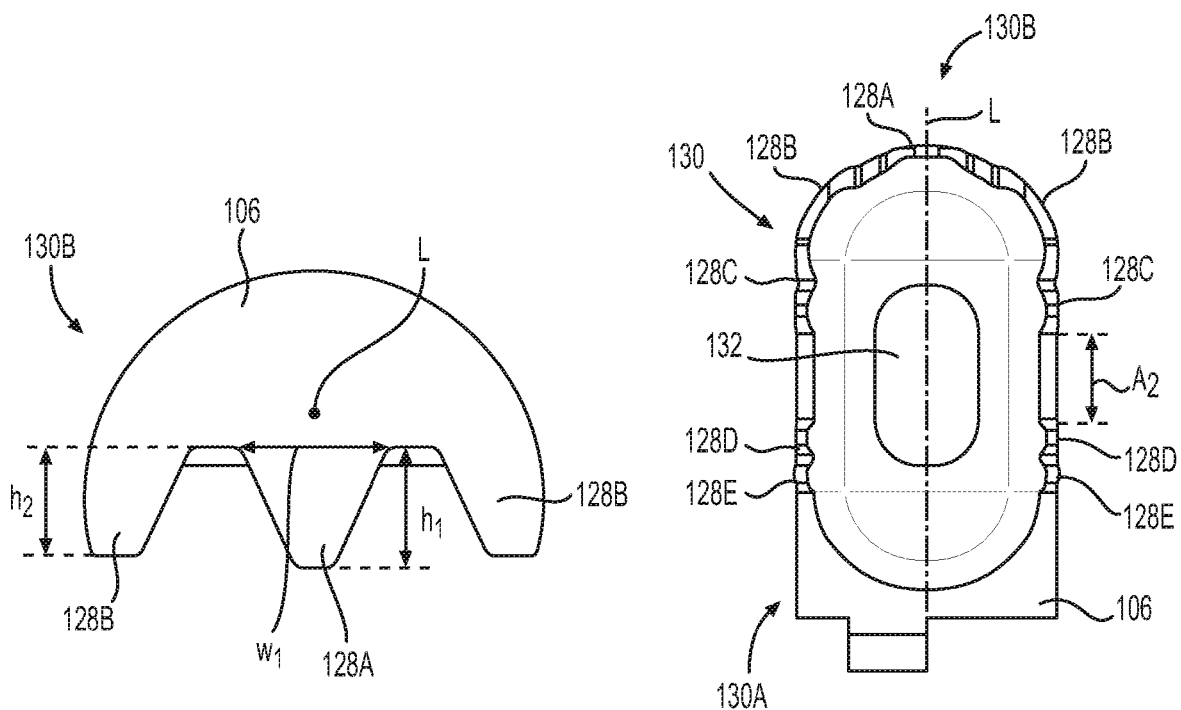
FIG. 10B  FIG. 10C

BIOPSY FORCEPS WITH SERRATED CUTTING JAWS

CROSS-REFERENCE TO RELATED APPLICATIONS

This patent application claims the benefit of priority under 35 U.S.C. § 119 to U.S. Provisional Patent Application No. 62/644,892 filed Mar. 19, 2018, which is incorporated by reference herein in its entirety.

TECHNICAL FIELD

The present disclosure relates generally to medical devices. More particularly, the disclosure relates to medical devices used, for example, for tissue collection during biopsy, and methods for using the devices.

BACKGROUND

Tissue samples are often examined to determine the presence of a pathological disorder. Endoscopic biopsy forceps may be used in conjunction with an endoscope for taking tissue samples from the human body for analysis. Often, the samples must be obtained from deep within the body at locations that are difficult to access using standard forceps jaws (e.g., tissue from areas accessible only via tortuous biliary paths). In some cases, the quality or quantity of tissue accessible by a physician using standard forceps may not be sufficient for accurate diagnosis. Furthermore, forceps jaws may be sometimes difficult to maneuver as needed to obtain bites tangential to an axis along which the forceps are inserted to the target area. The systems and methods described herein may alleviate this deficiency and one or more other deficiencies in the art. The scope of the current disclosure, however, is defined by the attached claims, and not by the ability to solve any specific problem.

SUMMARY

Aspects of the present disclosure relate to, among other things, a tissue collection device for biopsy applications. These aspects may include one or more of the features described below.

In one aspect of the present disclosure, a biopsy forceps device is disclosed. The device may include an end effector including opposing first and second jaws coupled together and configured to move from an open configuration to a closed configuration. Each of the first jaw and the second jaw may include an edge. At least portions of the edges of the first and second jaws may contact each other when the end effector is in the closed configuration. The edge of the first jaw may include a plurality of first teeth each having a base, and the edge of the second jaw may include a plurality of second teeth each having a base. The bases of two adjacent first teeth of the plurality of first teeth may be spaced apart from each other to form a first gap at the edge of the first jaw. And, the bases of two adjacent second teeth of the plurality of second teeth may be spaced apart from each other to form a second gap at the edge of the second jaw. The end effector in the closed configuration may define one or more windows between the edges of the first and the second jaws. And, at least one of the one or more windows may include at least a portion of one or both of the first gap and the second gap.

Various aspects of the present disclosure may additionally or alternatively include one or more of the following aspects: when the end effector is in the closed configuration, a first tooth of the two adjacent first teeth may be positioned on the second gap; when the end effector is in the closed configuration, a second tooth of the two adjacent second teeth may be positioned on the first gap; at least one first tooth of the plurality of first teeth has a generally triangular shape, at least one first tooth of the plurality of first teeth has a generally trapezoidal shape, at least one second tooth of the plurality of second teeth has a generally triangular shape, and at least one second tooth of the plurality of second teeth has a generally trapezoidal shape; the plurality of first teeth are arranged on the first jaw to be substantially symmetric about a longitudinal axis of the end effector, and the plurality of second teeth are arranged on the second jaw to be substantially symmetric about the longitudinal axis; each of the first jaw and the second jaw may include a substantially curved interior surface and a substantially convex outer surface, and wherein the substantially concave inner surfaces of the first and the second jaws together define a tissue receiving space when the end effector is in the closed configuration; at least one of the first jaw and the second jaw may include one or more apertures that extend between the substantially curved interior surface and the substantially convex outer surface of the respective jaw; at least one of the one or more apertures has a substantially elliptical shape, a substantially oval shape, or a substantially circular shape.

Various aspects of the present disclosure may also additionally or alternatively include one or more of the following aspects: each of the first jaw and the second jaw extends from a front end to a back end, and wherein (a) one or more first teeth of the plurality of first teeth that are positioned at the front end of the first jaw are bigger than one or more first teeth that are position at the rear end of the first jaw, and (b) one or more second teeth of the plurality of second teeth that are positioned at the front end of the second jaw are bigger than one or more second teeth that are positioned at the rear end of the second jaw; the plurality first teeth are arranged on the first jaw such that a plane passing through peaks of one or more first teeth positioned at the front end of the first jaw and one or more first teeth positioned at the rear end of the first jaw may be inclined with respect to a horizontal plane by an angle of about 2-10 degrees; the plurality second teeth are arranged on the second jaw such that a plane passing through peaks of one or more second teeth positioned at the front end of the second jaw and one or more second teeth positioned at the rear end of the second jaw may be inclined with respect to a horizontal plane by an angle of about 1-5 degrees; the plurality of first teeth and the plurality of second teeth may have a substantially same height; the one or more windows may include at least two windows separated by a tooth of the plurality of first teeth and the plurality of second teeth; the one or more windows may include (a) a first window formed between two teeth of the plurality of first teeth and the plurality of second teeth, and (b) a second window formed proximal to a proximal-most tooth of the plurality of first teeth and the plurality of second teeth; the end effector may extends along a longitudinal axis from a front end to a rear end, and wherein the one or more windows includes windows positioned on opposite sides of the longitudinal axis.

In another aspect of the present disclosure, a biopsy forceps device is disclosed. The device may include an end effector including opposing first and second jaws coupled together and configured to move from an open configuration to a closed configuration. Each of the first jaw and the second jaw may include an edge. At least portions of the edges of the first and second jaws may contact each other when the end effector is in the closed configuration. The edge of the first jaw may include a plurality of first teeth each having a base. The edge of the second jaw may include a plurality of second teeth each having a base. Wherein (a) at least one first tooth of the plurality of first teeth and one second tooth of the plurality of second teeth may include a generally triangular shape, (b) at least one first tooth of the plurality of first teeth and at least one second tooth of the plurality of second teeth may include a generally trapezoidal shape, (c) at least two adjacent first teeth of the plurality of first teeth may be spaced apart from each other to form a first gap on the edge of the first jaw, and (d) at least two adjacent second teeth of the plurality of second teeth may be spaced apart from each other to form a second gap on the edge of the second jaw. The end effector in the closed configuration may define one or more windows between the edges of the first and the second jaws. At least one of the one or more windows may include at least a portion of one or both of the first gap and the second gap.

Various aspects of the present disclosure may also additionally or alternatively include one or more of the following aspects: when the end effector is in the closed configuration, a first tooth of the at least two adjacent first teeth may be positioned on the second gap, and a second tooth of the at least two adjacent second teeth may be positioned on the first gap, and wherein the second tooth positioned on the first gap may include a generally trapezoidal shape; the end effector extends along a longitudinal axis from a front end to a rear end, and wherein the one or more windows may include two windows positioned on one side of the longitudinal axis and two windows positioned on an opposite side of the longitudinal axis.

In another aspect of the present disclosure, a biopsy forceps device is disclosed. The device may include an end effector including a longitudinal axis and opposing first and second jaws extending from a front end to a rear end, the first and second jaws being coupled together and configured to move from an open configuration to a closed configuration. Each of the first jaw and the second jaw may include an edge. At least portions of the edges of the first and second jaws contact each other when the end effector is in the closed configuration. The edge of the first jaw may include a plurality of first teeth, each having a base, arranged substantially symmetrically about the longitudinal axis. The edge of the second jaw may include a plurality of second teeth, each having a base, arranged substantially symmetrically about the longitudinal axis. The bases of at least two adjacent first teeth of the plurality of first teeth may contact each other. The bases of at least two adjacent second teeth of the plurality of second teeth may also contact each other. The bases of at least two adjacent first teeth of the plurality of first teeth may be spaced apart from each other to form a first gap on the edge of the first jaw. And, the bases of at least two adjacent second teeth of the plurality of second teeth may be spaced apart from each other to form a second gap on the edge of the second jaw. The end effector in the closed configuration may define multiple windows between the edges of the first and the second jaws. The multiple windows may include at least a first window and a second window symmetrically positioned on opposite sides of the longitudinal axis. Each of the first window and the second window may include at least a portion of one or both of the first gap and the second gap. The multiple windows may also include a third window and a fourth window symmetrically positioned on opposite sides of the longitudinal axis and located proximal to all the teeth of the plurality of first teeth and the plurality of second teeth.

Various aspects of the present disclosure may also additionally or alternatively include one or more of the following aspects: a height of each of the first and second windows may be about 3-8.5 mils, a width of each of the first and second windows may be about 3.5-7.5 mils, a height of each of the third and fourth windows may be about 4-8 mils, and a width of each of the third and fourth windows may be about 25-30 mils.

It may be understood that both the foregoing summary and the following detailed description are exemplary and explanatory only, neither being restrictive of the inventions claimed below.

BRIEF DESCRIPTION OF THE DRAWINGS

The accompanying drawings, which are incorporated in and constitute a part of this specification, illustrate exemplary embodiments that, together with the written description, serve to explain the principles of this disclosure.

FIGS. 10A-10C illustrate different views of the first jaw of FIG. 7;

DETAILED DESCRIPTION

Figure 1:
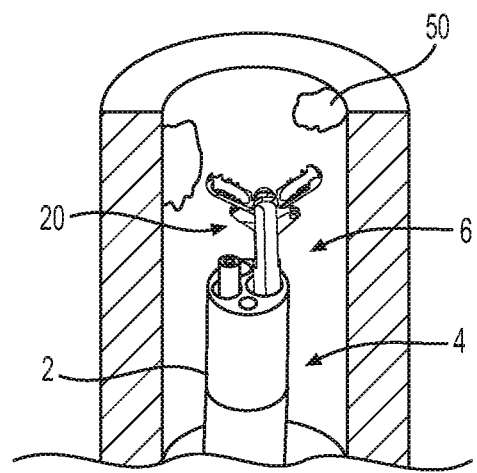
FIG. 1 is an exemplary tissue collection device of the current disclosure extending into the body of a patient through the distal end of an endoscope.

The present disclosure is now described with reference to an exemplary tissue collection device that may be used in an endoscopic biopsy procedure. However, it should be noted that reference to this particular procedure is provided only for convenience and not intended to limit the disclosure. A person of ordinary skill in the art would recognize that the concepts underlying the disclosed device and application method may be utilized in any suitable procedure, medical or otherwise. The present disclosure may be understood with reference to the following description and the appended drawings, wherein like elements are referred to with the same reference numerals.

Exemplary embodiments of the present disclosure describe a forceps assembly, or a device, that can be advanced through a working channel of an endoscope, including, for example, a SpyScope™ (or any other endoscopic device designed and/or sized for use with the forceps assembly, including but not limited to endoscopes, colonoscopies, duodenoscopes, endoscopic ultrasound (EUS) scopes, cystoscopes, ureteroscopes, bronchoscopes, catheters and the like), into a tissue tract. Embodiments of the disclosed device may increase the maneuverability of the device through tight curvatures within the working channels of the endoscopic devices as well as through a tortuous lumen of a living body. Exemplary embodiments of the biopsy forceps assembly include jaws with serrated cutting edges which may improve the grip of the jaws on target tissue surface without slip, and/or increase the volume of tissue that may be obtained using the device.

For ease of description, portions/regions/ends of the device and/or its components are referred to as proximal and distal ends/regions. It should be noted that the term "proximal" is intended to refer to ends/regions closer to a user of the device, and the term "distal" is used herein to refer to ends/regions further away from the user. Similarly, extends "distally" indicates that a component extends in a distal direction, and extends "proximally" indicates that a component extends in a proximal direction. Further, as used herein, the terms "about," "approximately" and "substantially" indicate a range of values within +/− 10% of a stated or implied value. Additionally, terms that indicate the geometric shape of a component/surface refer only to approximate shapes. For example, a tooth that is described as having a triangular or a trapezoidal shape indicates that the tooth has a generally triangular or a generally trapezoidal shape (e.g., vertices/corners of the triangular/trapezoidal shape may be sharp or rounded, its sides may be straight or curved, etc.).

FIG. 1 illustrates an exemplary embodiment of the disclosed tissue collection device ("device 20") positioned within the body of a patient ("body") proximate a region of tissue ("target tissue 50") that is desired to be collected for biopsy. In FIG. 1, device 20 is illustrated as extending into the body through distal end 6 of an endoscope 4. Endoscope 4 may include an elongate flexible tubular section 2 extending from a proximal end (not shown) positioned outside the body to the distal end 6 positioned proximate target tissue 50 within the body. Device 20 may be inserted into the body from the proximal end through a lumen (e.g., working channel) of endoscope 4. Without limitation, endoscope 4 may be any type of device (e.g. a SpyScope™, etc.) having a lumen that extends therethrough. In some embodiments, in place of endoscope 4, a hollow sheath, a colonoscope, a cystoscope, a ureteroscope, a bronchoscope, a catheter, or a like device may be used. For example, device 20 may be introduced into the body through the lumen of a hollow sheath. In some embodiments, device 20 may be used without an endoscope 4 or a sheath. For example, the distal end of device 20 may be directly inserted into the body (e.g., through an opening in the body) and pushed in until the distal end of device 20 is suitably positioned proximate target tissue 50.

Figure 2:
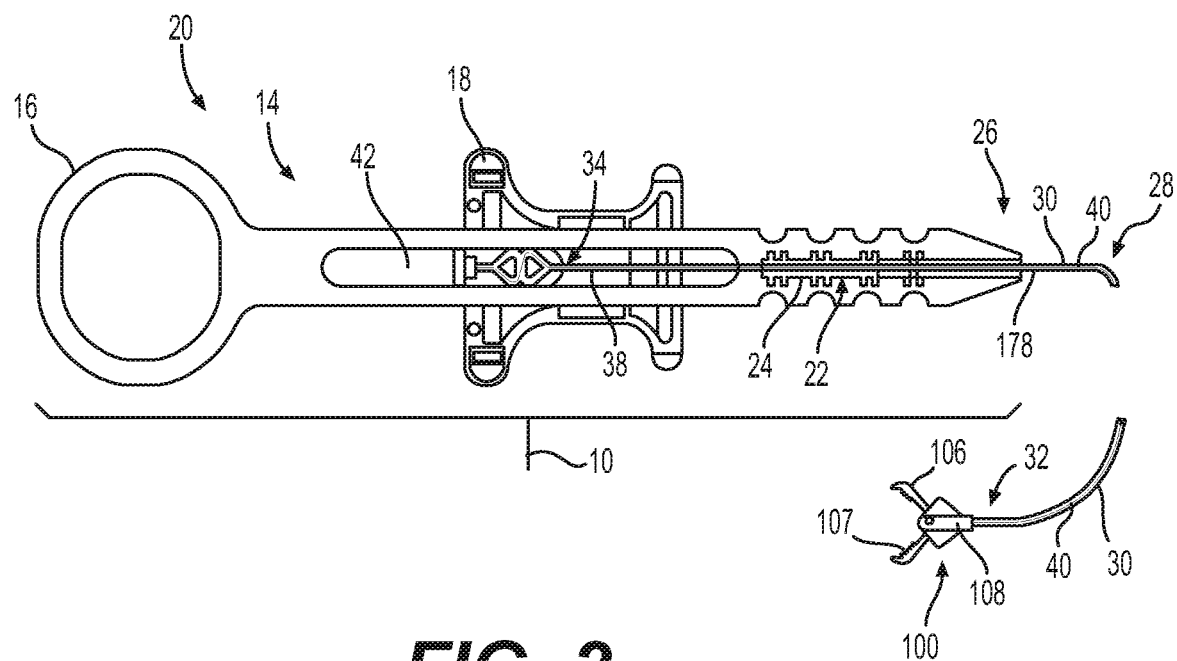
FIG. 2 illustrates an exemplary tissue collection device of FIG. 1.

FIG. 2 is an illustration of an exemplary tissue collection device 20. Device 20 includes a distal end effector assembly ("end effector 100") and a proximal actuator assembly ("actuator 10". An elongate member 30 connects distal end effector 100 to the proximal actuator 10. Actuator 10 includes a handle 14 with a thumb ring 16 and a spool 18. Spool 18 is movable along handle 14 and is sized and shaped to be grasped by a user. Elongate member 30 may include a flexible coil 28 and a coil retainer 22. Coil retainer 22 may be housed in a lumen 24 of handle 14. As illustrated in FIG. 2, coil retainer 22 may include flanges that mate with corresponding grooves in lumen 24 to prevent the longitudinal movement of coil retainer 22 within handle 14. A proximal end 26 of coil 28 is coupled (e.g., welded) to coil retainer 22. In some embodiments, coil retainer 22 may be formed integrally with coil 28. In an exemplary embodiment, elongate member 30 may be formed of a flexible, closely wound, stainless steel helical coil and may include a thin covering or coating, such as, for example, a layer of polytetrafluroethelene (PTFE). The coating may reduce friction between elongate member 30 and the working channel of endoscope 4 and enable device 20 to slide more easily within endoscope 4.

A control wire 40 extends through elongate member 30 from a proximal end 34 to a distal end 32. Control wire 40 may be sized and shaped to be slidably movable within elongate member 30. Control wire 40 and elongate member 30 may be sufficiently flexible to be passed through a working channel of endoscope 4 and passed along the body lumen along a tortuous path. In some embodiments, control wire 40 may be preferably formed of a material such as stainless steel exhibiting a torsional stiffness sufficient to transmit rotational force to its distal end. However, other suitable biocompatible materials (e.g., nitinol, etc.) may also be used for control wire 40. Although not a requirement, in some embodiments, control wire 40 may have a constant diameter along its length. In some embodiments, control wire 40 may including a coating (e.g., of PTFE) configured to reduce friction between control wire 40 and elongate member 30. Proximal end 34 of control wire 40 may be inserted into a hypotube 38. Hypotube 38 may be connected to spool 18 and configured to slide within coil retainer 22. In some embodiments, control wire 40 may be secured by a friction fit within hypotube 38 to prevent movement of control wire 40 relative to hypotube 38. Handle 14 may include a slot 42 that receives hypotube 38. An interior surface of spool 18 is configured to slide along the outside of handle 14 and slot 42. A user may slide spool 18 on handle 14 to actuate control wire 40.

Figure 3A:
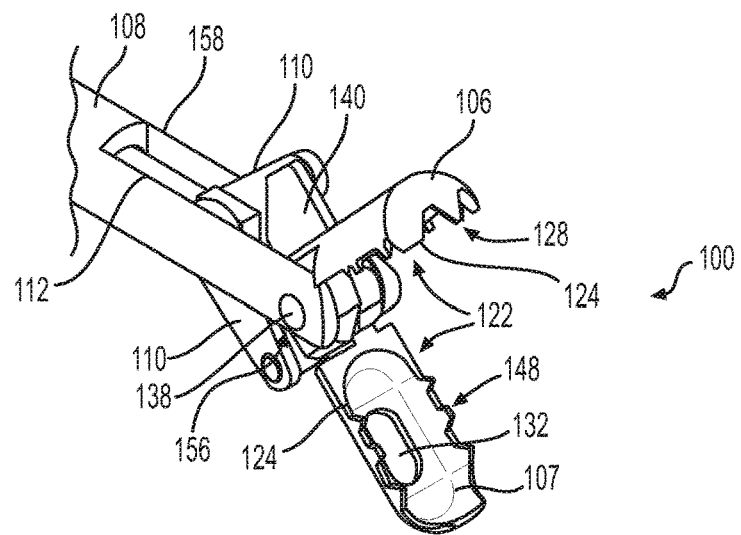
FIGS. 3A-3C illustrate different views of an exemplary end effector of the tissue collection device of FIG. 2.
Figure 3B:
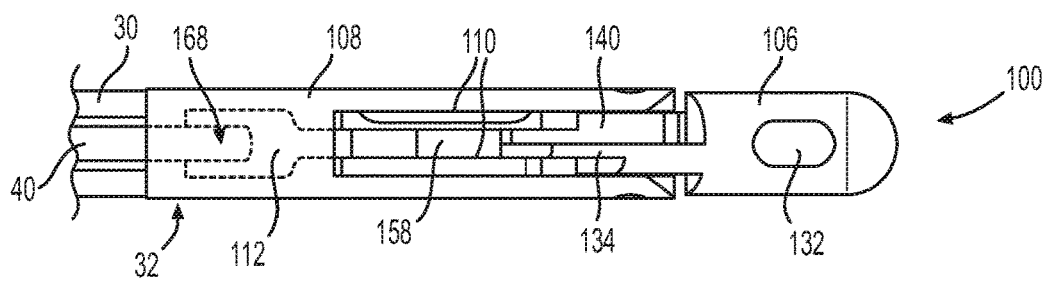

Control wire 40 may be coupled at its distal end 32 to the proximal end of a control wire attachment 112 (see FIG. 3B). Any suitable attachment method (such as, for example, welding, soldering, adhesives, etc.) may be used to couple control wire 40 to control wire attachment 112. In some embodiments, control wire 40 may include a taper at its distal end 32 to facilitate its connection with (e.g., insertion into) the proximal end of control wire attachment 112.

In general, device 20 may have any length. In some embodiments, to facilitate a wide range of applications and reach anatomical regions deep in the body, device 20 may have a length of about 270-300 centimeters (i.e., about 78.7-118.1 inches), or preferably about 270-290 centimeters (i.e., about 78.7-114.7 inches). However, this length is not a requirement, and in general, device 20 may have any suitable length. As noted above, the movable control wire 40 extends proximally from distal end 32 (i.e., extends in a proximal direction), within elongate member 30, to couple end effector 100 to the moveable spool 18. Movement of spool 18 relative to handle 14 moves control wire 40 within flexible coil 28 and transforms end effector assembly 100 between an open tissue-receiving configuration and a closed tissue-grasping configuration.

Figure 3C:
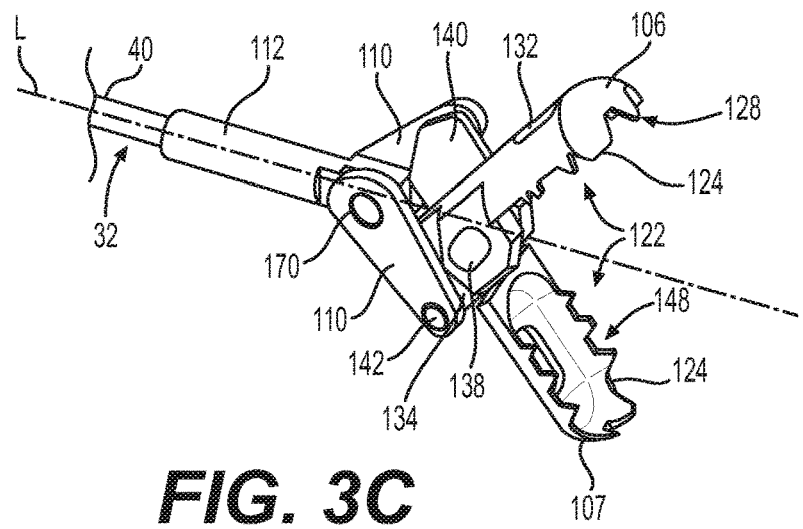

FIGS. 3A and 3B illustrate perspective and top views respectively of an embodiment of end effector 100 of device 20. End effector 100 includes first and second jaws 106, 107 rotatably coupled to a clevis 108 using a pivot pin 138. It should be noted that although first and second jaws 106, 107 are illustrated in a particular orientation (i.e., first jaw 106 as a top jaw and second jaw 107 as a bottom jaw), this is only exemplary. As would be recognized by a person skilled in the art, during a medical procedure, first and second jaws 106, 107 may have any orientation. FIG. 3C illustrates a perspective view of end effector 100 with clevis 108 removed. As best seen in FIG. 3C, a pair of links 110 connect the first and second jaws 106, 107 to core wire attachment 112.

Figure 4:
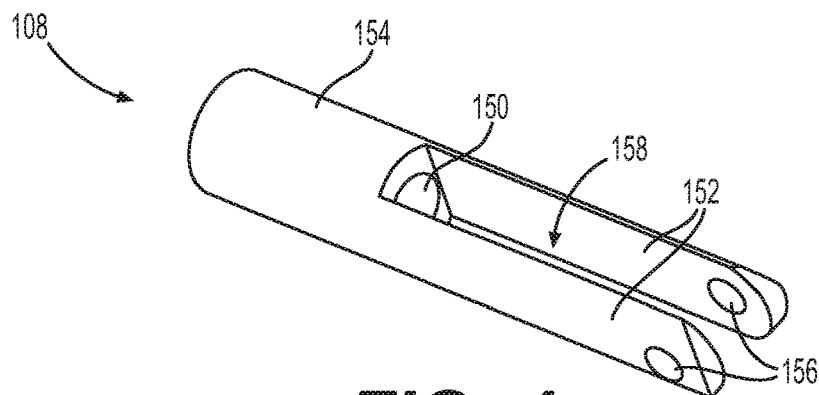
FIG. 4 illustrates an exemplary clevis of the end effector of FIGS. 3A-3C.
Figure 5:
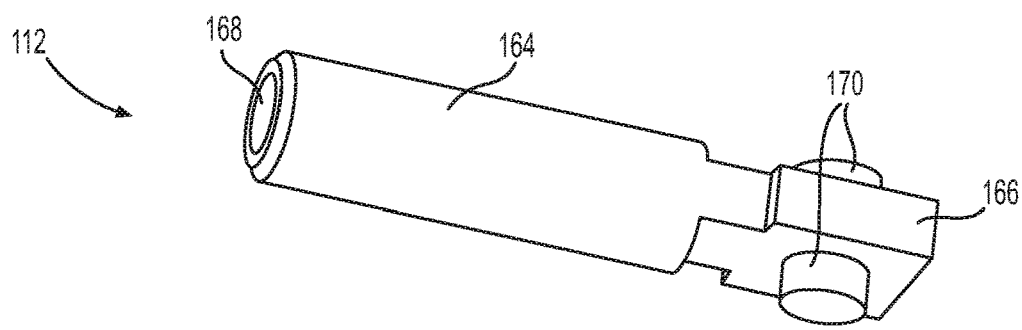
FIG. 5 illustrates an exemplary control wire attachment of the end effector of FIGS. 3A-3C.
Figure 6:
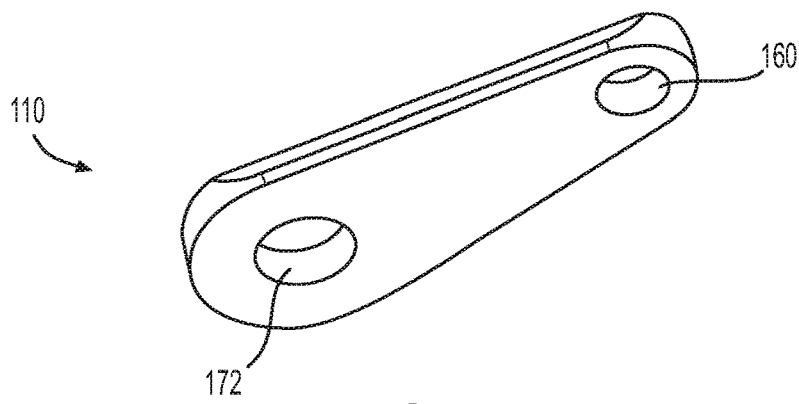
FIG. 6 illustrates an exemplary link of the end effector of FIGS. 3A-3C.
Figure 7:
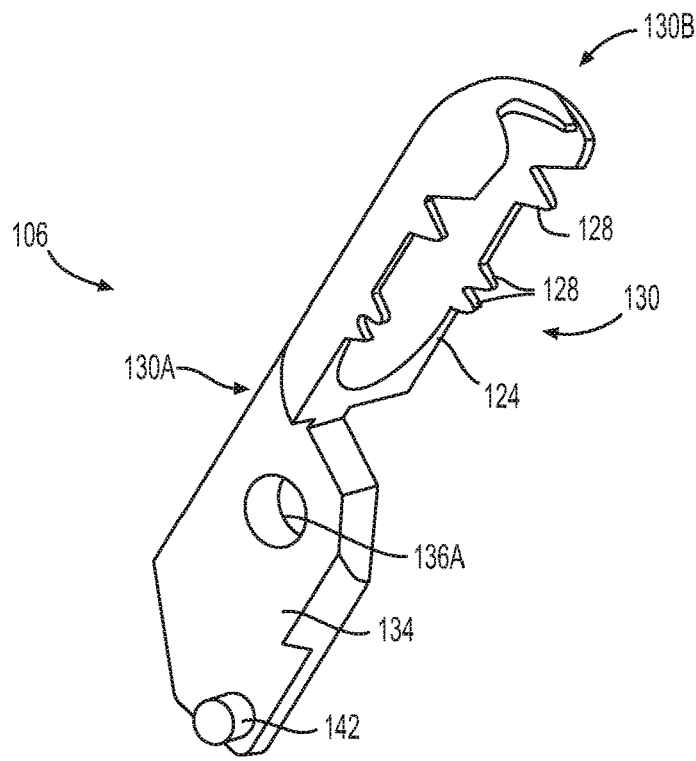
FIG. 7 illustrates an exemplary first jaw of the end effector of FIGS. 3A-3C.
Figure 8:
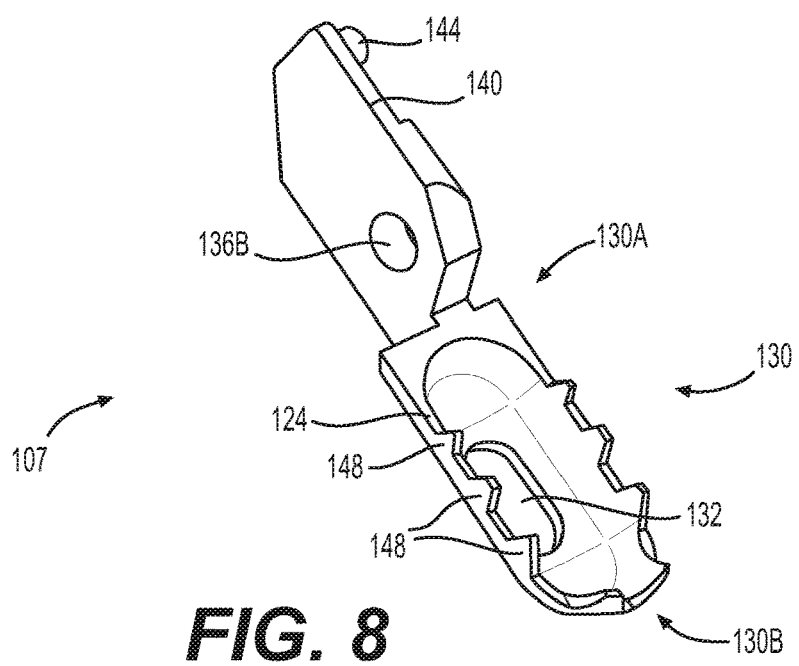
FIG. 8 illustrates an exemplary second jaw of the end effector of FIGS. 3A-3C.

FIG. 4 illustrates an embodiment of clevis 108, FIG. 5 illustrates an embodiment of core wire attachment 112, FIG. 6 illustrates an embodiment of link 110, FIG. 7 illustrates an embodiment of first jaw 106, and FIG. 8 illustrates an embodiment of second jaw 107. In the discussion below, reference will be made to FIGS. 3A-8.

As best seen in FIG. 4, clevis 108 includes a generally cylindrical proximal portion 154 with a pair of arms 152 extending distally (i.e., extending in a distal direction) therefrom. A jaw receiving space 158 is defined between the pair of arms 152. A central lumen 150 extends through proximal portion 154 of clevis 108. Lumen 150 is sized and shaped to receive control wire attachment 112 therein. Each arm 152 of clevis 108 has a generally curved outer surface and a generally flat inner surface and includes a pivot pin hole 156 to receive a pivot pin 138 therein (see FIGS. 3A and 3C). As best seen in FIGS. 3A and 3B, jaw receiving space 158 (defined between the flat inner surfaces of the two arms 152) of clevis 108 is sized to receive tangs 134, 140 provided on the proximal ends of the first and second jaws 106, 107 (see FIGS. 7 and 8).

As shown in FIG. 7, in first jaw 106, the proximal tang 134 includes a pivot hole 136A that is sized and shaped to receive pivot pin 138 therethrough. As shown in FIG. 8, tang 140 of second jaw 107 also defines a similarly sized pivot hole 136B for receiving pivot pin 138. Pivot pin 138 is configured to extend through the pivot holes 136A, 136B transverse to a central longitudinal axis L of end effector 100 (see FIG. 3C). First and second jaws 106, 107 further include actuating pins 142, 144, respectively, extending from an outer surface of tangs 134, 140. Actuating pins 142, 144 are sized and shaped to be received within corresponding distal through-holes 160 (see FIGS. 3C and 6) of each link 110. Actuating pins 142, 144 are located proximally of the pivot holes 136A, 136B, and are positioned such that, when the jaws 106, 107 are assembled, pins 142, 144 face each other. As best seen in FIGS. 3A and 3C, pivot pin 138 extends through pivot pin holes 156 of the two arms 152 (of clevis 108) and the pivot holes 136A, 136B of the first and second tangs 134, 140 to pivotably (or rotatably) couple the first and second jaws 106, 107 to clevis 108. Rotation of the first and second jaws 106, 107 about pivot pin 138 transforms end effector 100 between its open tissue-receiving and closed tissue-grasping configurations.

Control wire attachment 112 extends through the clevis lumen 150 and connects to a distal end 32 of control wire 40 (see FIG. 3B). With reference to FIG. 5, control wire attachment 112 extends from a proximal end to a distal end and includes a proximal part 164 and a distal part 166. The proximal part 164 is substantially cylindrical and defines a central blind hole 168 open at the proximal end. The distal part 166 includes opposing generally flat lateral surfaces with each lateral surface including a link pin 170 extending laterally therefrom. As best seen in FIG. 3B, the distal end of control wire 40 is inserted into blind hole 168 of core wire attachment 112 and fixedly connected (e.g., by welding, etc.) thereto.

As best seen in FIG. 3C, a pair of links 110 couple control wire attachment 112 to the first and second jaws 106, 107. In some embodiments, the pair of links 110 may be substantially similar in shape. With reference to FIG. 6, each link 110 defines a proximal through-hole 172 at its proximal end and a distal through-hole 160 at its distal end. As best seen in FIG. 3C, the two links 110 are positioned on the two opposing lateral surfaces on the distal part 166 (see FIG. 5) of control wire attachment 112, with link pin 170 (that extends from each lateral surface of control wire attachment 112) inserted into the proximal through-hole 172 of the corresponding link 110 to rotatably couple the two links 110 to control wire attachment 112. The distal through-hole 160 of each link 110 receives the actuating pin 142, 144 of the corresponding one of the first and second jaws 106, 107 to rotatably couple the jaws 106, 107 to the links 110. With reference to FIG. 3C, when control wire 40 is moved distally by moving spool 18 distally on handle 14, the control wire attachment 112 is moved distally along longitudinal axis L. When control wire attachment 112 moves distally, the proximal end of each link 110 pivots about link pin 170 and rotates the distal end of that link 110 away from longitudinal axis L. Thus, when control wire attachment 112 moves distally, the distal ends of both links 110 rotate in opposite directions away from longitudinal axis L and force the first and second jaws 106, 107 to rotate about pivot pin 138 to its open configuration. Conversely, when control wire attachment 112 is moved proximally (by moving spool 18 proximally on handle 14), the links 110 are pulled proximally such that the two links 110 and the first and second jaws 106, 107 pivot about their respective pins to rotate the first and second jaws 106, 107 toward each another (i.e., into the closed configuration of end effector 100).

It should be noted that, although a specific end effector actuation mechanism (e.g., control wire 40 coupling moveable spool 18 to end effector 100, etc.) is described above, this is only exemplary. Other embodiments of device 20 may have other types of actuation mechanisms configured to transform end effector 100 between its open and closed configurations (i.e., actuate end effector 100). As known to people skilled in the art, there are many types of actuation mechanisms known in the art that may be used to actuate end effector 100. In general, without limitation, any now-known or later-developed actuation mechanism suitable to actuate end effector 100 may be used with device 20.

First and second jaws 106, 107 of end effector 100 may be made of any biocompatible material. In some embodiments, first and second jaws 106, 107 may be micromachined (or fabricated in another manner) from stainless steel, sheet metal, a stiffer aluminum alloy (such as, for example, 6000 or 7000 series aluminum alloy, etc.), LCP or other equivalent grades of plastic. It is also contemplated that jaws 106, 107 (and other components of device 20 may be made of other suitable materials, such as, for example, nitinol, polymer, nylon, etc. With reference to FIGS. 7 and 8, first and second jaws 106, 107 include a generally cup-shaped region 130 that extends from a proximal end 130A to a distal end 130B. Tang 134 of first jaw 106 extends proximally from the proximal end 130A of cup-shaped region 130, and tang 140 of second jaw 107 extends proximally from proximal end 130A of cup-shaped region 130 of second jaw 107. Cup-shaped regions 130 of both first and second jaws 106, 107 have a generally convex outer surface and a generally concave inner surface. When the first and second jaws 106, 107 are coupled together (see FIGS. 3A and 3C), their generally concave inner surfaces together define a tissue-receiving space 122 therebetween. The outer perimeter edges of the cup-shaped regions 130 of the first and second jaws 106, 107 include tissue cutting edges 124 that are configured to at least partially mate with one another when the jaws 106, 107 are in a closed configuration. It should be emphasized that, when the jaws 106, 107 are in a closed configuration, some portions of the edges 124 (of the two jaws 106, 107) may be in a mating relationship while other portions of the edges 124 may be in a non-contacting relationship. Teeth 128 (or serrations) are arranged on the tissue cutting edge 124 of the first jaw 106, and teeth 148 are arranged on the tissue cutting edge 124 of the second jaw 107. The geometry and arrangement of teeth 128, 148 on the first and second jaws 106, 107 will be described later.

Figure 9A:
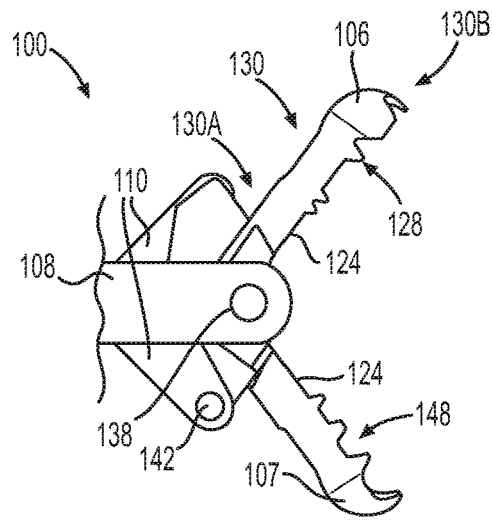
FIG. 9A illustrates a side view of the end effector of FIGS. 3A-3C in an open configuration.
Figure 9B:
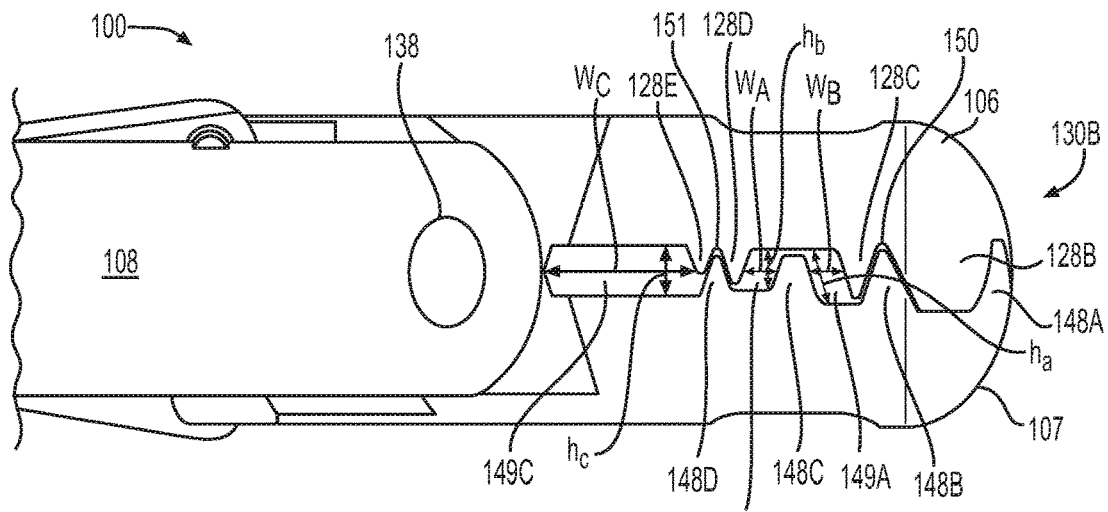
FIG. 9B illustrates a side view of the end effector of FIGS. 3A-3C in a closed configuration.
Figure 9C:
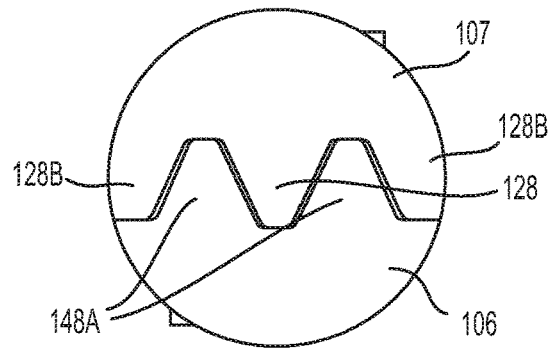
FIG. 9C illustrates a front view of the end effector of FIGS. 3A-3C in a closed configuration.

To obtain a tissue sample for biopsy (e.g., sample of target tissue 50 of FIG. 1), end effector 100 of device 20 is positioned adjacent to target tissue 50 (on a tissue wall of a body cavity), and spool 18 (see FIG. 2) is moved in a distal direction. When spool 18 is moved distally, as described previously, the two links 110 rotate about link pin 170, to cause the first and second jaws 106, 107 to rotate about pivot pin 138 to the open configuration of end effector 100 (see FIG. 3A). FIGS. 9A and 9B illustrate side views of end effector 100 in the open and closed configurations, respectively. And FIG. 9C is a front view of the end effector 100 in the closed configuration. With the first and second jaws 106, 107 open, end effector 100 is pushed toward and/or against target tissue 50, and the spool 18 is moved proximally to close the jaws 106, 107 (i.e., to transform end effector 100 to its closed configuration). As the jaws 106, 107 rotate towards each other, a portion of the target tissue 50 is captured in the tissue-receiving space 122 between the jaws 106, 107. As the two jaws 106, 107 move closer to each other, teeth 128, 148 on the jaws 106, 107 pierce and anchor within the target tissue 50, and increase the volume of target tissue 50 captured in tissue-receiving space 122 (sometimes referred to as a tissue "bite"). First and second jaws 106, 107 are then closed (see FIGS. 9B and 9C) by further moving spool 18 proximally. As the first and second jaws 106, 107 close, the cutting edges 124 of the first and second jaws 106, 107 sever the tissue captured between the first and second jaws 106, 107. Device 20 is then withdrawn proximally from endoscope 4 (see FIG. 1), and the severed tissue is retrieved from between the first and second jaws 106, 107. In an exemplary embodiment, end effector 100 may have a rigid portion having a length of about 2-6 mm (or preferably about 3-5 mm, or more preferably about 3.5 mm) with a length of clevis 108 of about 1-4 mm (preferably about 1.5-3.5 mm) to allow end effector 100 to easily pass through acute curvatures within a body.

Figure 11A:
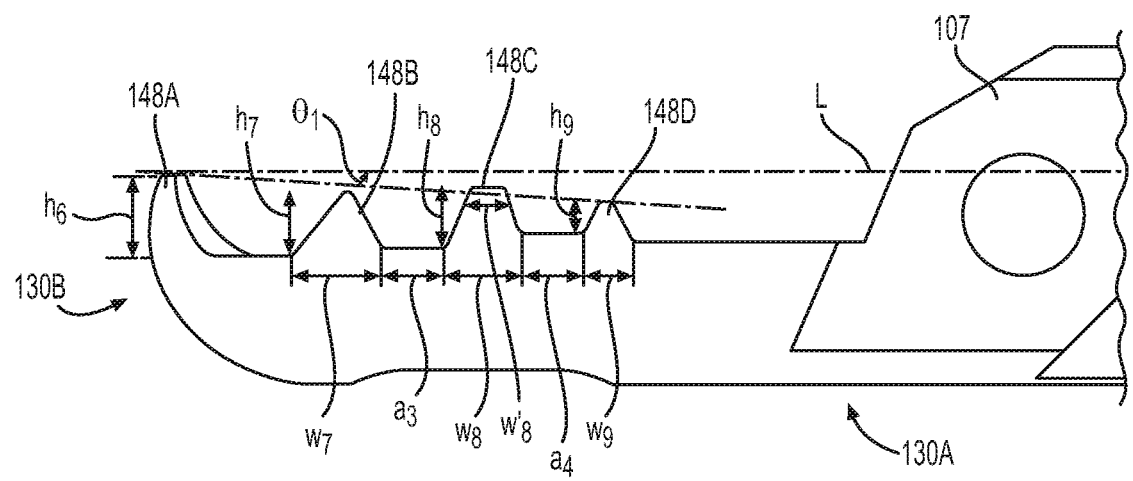
FIGS. 11A-11C illustrate different views of the second jaw of FIG. 8
Figure 11B:
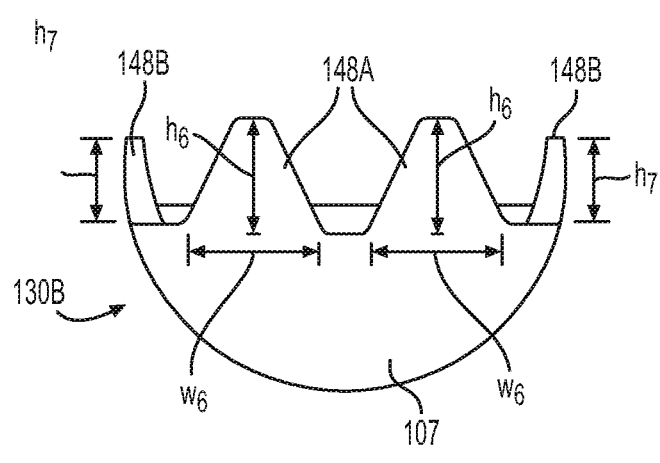
Figure 11C:
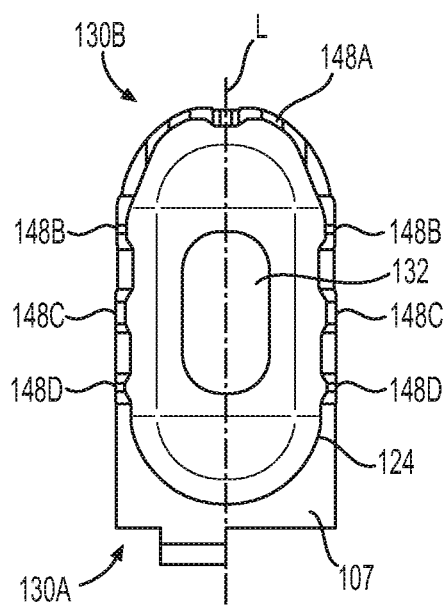

FIGS. 10A, 10B, and 10C are side, front, and top views of an exemplary first jaw 106, and FIGS. 11A, 11B, and 11C are side, front, and top views of an exemplary second jaw 107. As best seen in FIGS. 10C and 11C, the cup-shaped region 130 of each of the first and second jaws 106, 107 includes a fenestration hole or an aperture 132 that extends from the convex outer surface to the concave inner surface of the respective jaw (see also FIG. 3C). During use, aperture 132 enables fluids (e.g., bile fluids) from the bite of tissue captured in the tissue-receiving space 122 (between the jaws 106, 107) to escape. Allowing these fluids to escape may increase the volume of tissue that may be captured by device 20. Allowing the fluids to escape through aperture 132 may also prevent pressure buildup in the tissue-receiving space 122 and avoid inducing trauma (e.g., crushing) to the captured tissue. In some embodiments, aperture 132 may be positioned symmetrically (or substantially symmetrically) about longitudinal axis L. See FIGS. 10C and 11C. Although not a requirement, in some embodiments, aperture 132 may have an oval or an elliptical shape with its major axis (or long axis) extending along, or parallel to, longitudinal axis L. In general, aperture 132 may have any size. In some embodiments, an increased size of aperture 132 (within limits) may improve the tissue capture performance of end effector 100, e.g., allowing for an increased sample size and/or reducing crushing of the tissue sample. For example, the aperture 132 may extend over a surface area of the cup-shaped region 130 to provide drainage and to minimize or reduce crushing (e.g., trauma) to the tissue sample received in the tissue-receiving space 122 when the first and second jaws 106, 107 are closed. In some embodiments, the minor axis of aperture 132 may be between about 0.010 inches to 0.020 inches (i.e., about 10-20 mils), and its major axis may be between 0.020 inches to about 0.040 inches (i.e., about 20-40 mils). In some embodiments, the size of aperture 132 may be about 15 mils×30 mils (minor axis×major axis). In some embodiments, aperture 132 may be provided on only one of jaws 106, 107. Also, in some embodiments, a different shaped aperture 132 (e.g., similar to apertures 232, 332, 432 described later) and/or a different number of apertures (e.g., 2, 3, 4, etc.) may be provided in one or both jaws 106, 107.

Exemplary configurations (shape, profile, arrangement, etc.) of teeth 128, 148 of the first and second jaws 106, 107 will now be described. As best seen in FIGS. 10C and 11C (and also evident from the side views of FIGS. 10A and 11A), teeth 128 of first jaw 106, and teeth 148 of second jaw 107, are arranged symmetrically (or substantially symmetrically) about longitudinal axis L in the respective jaw. In some embodiments, as best seen in FIGS. 9B and 9C, teeth 128 of the first jaw 106 and teeth 148 of the second jaw 107 are offset from each other such that the tips or peaks of teeth 128 (of first jaw 106) fit within the valleys of teeth 148 (of second jaw 107), and vice versa. This offset fit of teeth 128, 148 of the first and second jaws 106, 107 enables end effector 100 to obtain a clean cut of the target tissue 50 without damaging either the tissue or the first and second jaws 106, 107.

Teeth 128 of first jaw 106 includes multiple teeth arranged along the tissue cutting edge 124 of the first jaw 106. With specific reference to FIGS. 10A-10C, arranged from distal end 130B (of cup-shaped region 130) towards proximal end 130A, teeth 128 includes a first tooth 128A and two each of second, third, fourth, and fifth teeth 128B, 128C, 128D, and 128E. That is, in first jaw 106, first tooth 128A is the distal-most tooth (positioned closest to the distal end 130B) and the pair of fifth teeth 128E are the proximal-most teeth (positioned closest to the proximal end 130A). In some embodiments, the height of teeth 128 in first jaw 106 may progressively decrease from the distal end 130B to the proximal end 130A. That is, in general, the height of teeth that are positioned closer to the distal end 130B may be higher than the teeth that are positioned closer to the proximal end 130A. In some embodiments, as best seen in FIG. 10A, the heights of teeth 128 in first jaw 106 (i.e., first, second, third, fourth, and fifth teeth 128A, 128B, 128C, 128D, and 128E) may be such that, a plane passing through the peaks or tips of the distal-most tooth/teeth (e.g., first tooth 128A) and the proximal-most tooth/teeth (e.g., fifth teeth 128E) is inclined with respect to a horizontal plane (e.g., a plane parallel to longitudinal axis L) by an angle $\theta_1$. Note that, as also illustrated in FIG. 10A, in general, the tips of the teeth positioned in between the distal-most and proximal-most teeth (i.e., second, third, and fourth teeth 128B, 128C, 128D) may be positioned above or below the plane passing through the tips of the distal-most and proximal-most teeth. It is also contemplated that, in some embodiments, the tips of all (or substantially all) the teeth in first jaw 106 may be positioned substantially on the plane passing through the tips of the distal-most and proximal-most teeth. In some embodiments, angle $\theta_1$ may be about 2-10 degrees, or 4-8 degrees (or preferably about 5-7 degrees, or more preferably about 6 degrees). In some embodiments, all the teeth of first jaw 106 may be of the same height (i.e., angle $\theta_1 \cong 0$ degrees). First tooth 128A is positioned at the distal-most end of cup-shaped region 130. As best seen in FIG. 10B, first tooth 128A may have a generally triangular profile having a height $h_1$ and width $w_1$ at its base. In general teeth 128 may be of any height (varying from distal end 130B to proximal end 130A). In some embodiments, height $h_1$ may be between about 8-12 mils (or preferably about 9-11 mils) and width $w_1$ may be between about 10-14 mils (preferably about 11-13 mils). As explained previously, generally triangular profile refers only to the approximate shape of the tooth. For example, first tooth 128A may have an approximately triangular shape with sharp or rounded corners and straight or curved sides. Therefore, at its tip or peak, first tooth 128A may be pointed (and sharp), rounded, or flat-topped.

The two second teeth 128B may have a similar shape and may be positioned on either side of first tooth 128A substantially symmetrically about longitudinal axis L. It should be noted that, in some embodiments, each second tooth 128B may be positioned adjacent to first tooth 128A (e.g., with no or minimal gap between their bases). In some embodiments, there may be a gap between the base of each second tooth 128B and the base of first tooth 128A. In some embodiments, second tooth 128B may have a generally trapezoidal shape with a height $h_2$, a width $w_2$ at its base, and a width $w_2'$ at its peak. However, it is also contemplated that, in some embodiments, second tooth 128B may have a different shape (e.g., generally triangular shape). In some embodiments, height $h_2$ may be about 7-11 mils (or preferably about 8-10 mils), width $w_2$ may be about 7-12 mils (or preferably about 8-10 mils), and width $w_2'$ may be smaller than $w_2$ and may be about 2-8 mils (or preferably about 4-7 mils). As described previously, the corners of the generally trapezoidal second teeth 128B may be sharp or rounded, and its sides may be straight or curved. Each third tooth 128C of the two third teeth 128C may be positioned proximal to each second tooth 128B. See FIGS. 10A and 10C. The two third teeth 128C may be arranged substantially symmetrically about longitudinal axis L and have a substantially similar shape. In some embodiments, each third tooth 128C may have a generally triangular shape with a height $h_3$ and a width $w_3$. However, it is also contemplated that, in some embodiments, third teeth 128C may have a different shape (e.g., generally trapezoidal shape or a rounded shape). In some embodiments, height $h_3$ may be about 4-8 mils (or preferably about 5-7 mils), and width $w_3$ may be about 5-9 mils (or preferably about 6-8 mils). In some embodiments, as best seen in FIG. 10A, second and third teeth 128B, 128C are positioned such that, at their base, the two teeth abut.

The two fourth teeth 128D and the two fifth teeth 128E are positioned proximal to the third teeth 128C. The two fourth teeth 128D may be similar in shape and arranged substantially symmetrically about longitudinal axis L. See FIGS. 10A and 10C. Similarly, the two fifth teeth 128E may be similar in shape and arranged substantially symmetrically about longitudinal axis L. As seen in FIG. 10A, third and fourth teeth 128C, 128D may be positioned such that, at their base, they are separated by a distance $a_2$. In some embodiments, distance $a_2$ may be about 13-17 mils (or preferably about 14-16 mils). Fifth tooth 128E is positioned proximal to fourth tooth 128D and arranged such that they abut at their base. See FIG. 10A. Each of fourth tooth 128D and fifth tooth 128E may have a generally triangular shape. However, it is also contemplated that, in some embodiments, each fourth tooth 128D may have a different shape (e.g., generally trapezoidal or another shape). Fourth tooth 128D may have a height $h_4$ and width $w_4$, and fifth tooth 128E may have a height $h_5$ and width $w_5$. In some embodiments, height $h_4$ may be about 2-6 mils (or preferably about 3-5 mils) and width $w_4$ may be about 4-8 mils (or preferably 5-7 mils). In some embodiments, $h_5$ may be smaller than $h_4$, and $w_5$ may be smaller than $w_4$. In some embodiments, height $h_5$ may be about 2-5 mils (or preferably about 2.5-4 mils), and width $w_5$ may be about 3-7 mils (or preferably 4-5.5 mils).

With reference to FIGS. 11A-11C, teeth 148 of second jaw 107 includes two each of first, second, third, and fourth teeth 148A, 148B, 148C, and 148D arranged from its distal end 130B towards proximal end 130A. Similar to teeth 128 of first jaw 106, first, second, third, and fourth teeth 148A, 148B, 148C, and 148D may progressively decrease in height from distal end 130B to proximal end 130A. That is, in general, the height of teeth 148 that are positioned closer to the distal end 130B may be higher than the teeth that are positioned closer to the proximal end 130A. In some embodiments, as best seen in FIG. 11A, the heights of teeth 148 in first jaw 107 may be such that, a plane passing through the peaks or tips of the distal-most tooth/teeth (e.g., first teeth 148A) and the proximal-most tooth/teeth (e.g., fourth teeth 148D) is inclined with respect to a horizontal plane (e.g., a plane parallel to longitudinal axis L) by an angle $\theta_2$. Note that, as also illustrated in FIG. 11A, in general, the tips of the teeth positioned in between the distal-most and proximal-most teeth (i.e., second and third 148B, 148C) may be positioned above or below the plane passing through the tips of the distal-most and proximal-most teeth. It is also contemplated that, in some embodiments, the tips of all (or substantially all) the teeth in second jaw 107 may be positioned substantially on the plane passing through the tips of the distal-most and proximal-most teeth. In some embodiments, angle $\theta_2$ may be about 1-5 degrees (or preferably about 2-4 degrees, or more preferably about 3 degrees). As best seen in FIG. 11B and 11C, the two first teeth 148A may be arranged substantially symmetric to longitudinal axis L. In general, each of the two first teeth 148A may be sized such that, in the closed configuration of end effector 100, each first tooth 148A of second jaw 107 fits into the space between the first and second teeth 128A, 128B of first jaw 106 (see FIG. 9C). In some embodiments, each first tooth 148A (of second jaw 107) fits into the space between the first and second teeth 128A, 128B (of first jaw 106) such that the external surfaces of these teeth form a closed, or a substantially continuous, surface without a substantial gap (e.g., ≤ about 1 mil, ≤ about 0.45 mils, etc.) between the individual teeth. That is, the shape of each first tooth 148A of second jaw 106 may substantially correspond with the shape of the space between the first and second teeth 128A, 128B of first jaw 106. And, the shape of first tooth 128A of first jaw 106 may correspond with the shape of the space between the two first teeth 148A of second jaw 107. In some embodiments, each first tooth 148A may have a height $h_6$ and width $w_6$. In some embodiments, height $h_6$ may be about 7-11 mils (or preferably about 8-10 mils) and $w_6$ may be about 10-14 mils (or preferably about 11-13 mils). In some embodiments, the side surfaces between the tips and bases (or portions of these side surfaces) of teeth 148B on the one hand, and teeth 128B, 128C on the other hand, contact when in the closed configuration, and leave a small gap 150 (e.g., for clearance) between the tips of teeth 148B and bases (or roots) of teeth 128B, 128C, as shown in FIG. 9B.

The two second teeth 148B of second jaw 107 may have a similar shape and may be positioned substantially symmetrically about longitudinal axis L. As best seen in FIG. 11A, second tooth 148B may have a substantially triangular shape with a height $h_7$ and a width $w_7$. In some embodiments, height $h_7$ may be about 4-9 mils (or preferably about 5.5-7.5 mils) and width $w_7$ may be about 8-12 mils (or preferably 9-11 mils). When end effector 100 is in its closed configuration, each second tooth 148B may fit into the space between the second and third teeth 128B, 128C of first jaw 106 (see FIG. 9B). In some embodiments, as illustrated in FIG. 9B, the external surfaces of teeth 128B, 148B, and 128C may form a closed surface (or substantially continuous) without a substantial gap between the individual teeth. That is, the shape of each second tooth 148B of second jaw 106 may substantially correspond with the shape of the space between the second and third teeth 128B, 128C of first jaw 106. And, the shape of each second tooth 128B of first jaw 106 may correspond to the shape of the space between the first and second teeth 148A, 148B of second jaw 107. See FIG. 9B. In some embodiments, the side surfaces between the tips and bases (or portions of these side surfaces) of teeth 148B on the one hand, and teeth 128B, 128C on the other hand, contact when in the closed configuration, and leave a small gap 150 between the tips of teeth 148B and bases (or roots) of teeth 128B, 128C, as shown in FIG. 9B.

The two third teeth 148C may be positioned proximal to the second teeth 148B and arranged substantially symmetrically about longitudinal axis L. As illustrated in FIG. 11A, at their base, each third tooth 148C may be separated from its neighboring second tooth 148B by a distance $a_3$. In some embodiments, distance $a_3$ may be between about 5-9 mils (or preferably about 6-8 mils). The two third teeth 148C may have a substantially similar generally trapezoidal shape with a height $h_8$, a width $w_8$ at its base, and a width $w_8'$ at its peak. However, it is also contemplated that, in some embodiments, each third tooth 148C may have a different shape (e.g., generally triangular or another shape). In some embodiments, height $h_8$ may be about 4-8 mils (or preferably about 5-7 mils), width $w_8$ may be about 6-10 mils (or preferably about 7.5-9.5 mils), and $w_8'$ may smaller than $w_8$ and may be about 2-8 mils (or preferably about 3-7 mils). When end effector 100 is in its closed configuration, each third tooth 148C may fit into the space between the third and fourth teeth 128C, 128D of first jaw 106 (see FIG. 9B). As illustrated in FIG. 9B, the sizes (e.g., heights, widths) of teeth 128C, 148C, and 128D, and their spacing (e.g., distances $a_2$, $a_3$, $a_4$) are such that, when end effector 100 is its closed configuration, side windows 149A, 149B (or gaps) having widths $w_A$ and $w_B$, and heights $h_A$ and $h_B$, are formed between these teeth. In general, side windows 149A and 149B may have the same or different widths and/or heights. In some embodiments, widths $w_A$ and $w_B$ may be about 3.5-7.5 mils (or preferably about 4.5-6.5 mils) (same or different values). In some embodiments, side windows 149A and 149B may have heights ($h_A$, $h_B$) between about 3-8.5 mils (same or different heights). In some embodiments, height $h_A$ may be about 4.5-8.5 mils (or preferably about 5.5-7.5 mils), and height $h_B$ may be about 3-7 mils (or preferably about 4-6 mils). It should be noted that the heights of teeth (128 and 148) disclosed herein are perpendicular heights (i.e., not along the slope of a tooth). Each window 149A, 149B may be substantially parallelogram shaped. During evaluation, it was found that these side windows 149A, 149B assist in acquiring more tissue during tangential tissue acquisition and lead to better quality of the acquired tissue.

Fourth tooth 148D is positioned proximal to the third tooth 148C. As illustrated in FIG. 11A, at their base, fourth tooth 148D is spaced apart from third tooth 148C by a distance $a_4$. In some embodiments, distance $a_4$ may be about 6-10 mils (or preferably about 7-9 mils). The two fourth teeth 148D may be similar in shape and arranged substantially symmetrically about longitudinal axis L. Each fourth tooth 148D may have a generally triangular shape with a height $h_9$ and width $w_9$. However, it is also contemplated that, in some embodiments, each fourth tooth 148D may have a different shape (e.g., generally trapezoidal or another shape). In some embodiments, height $h_9$ may be about 3-6 mils (or preferably about 4-5.5 mils), and width $w_9$ may be about 4-7 mils (or preferably about 5-6 mils). As illustrated in FIG. 9B, when end effector 100 is in its closed configuration, fourth tooth 148D may fit into the space between the fourth and fifth teeth 128D, 128E of first jaw 106 such that the external surfaces of these teeth (i.e., teeth 128D, 148D, and 128E) form a closed surface (or substantially continuous surface) without a substantial gap (e.g., ≤ about 1 mil, ≤ about 0.45 mils, etc.) between the individual teeth. That is, the shape of fourth tooth 148D of second jaw 106 may substantially correspond with the shape of the space between the fourth and fifth teeth 128D, 128E of first jaw 106. In some embodiments, the side surfaces between the tips and bases (or portions of these side surfaces) of teeth 148D on the one hand, and teeth 128D, 128E on the other hand, contact when in the closed configuration, and leave a small gap 151 between the tips of teeth 148D and bases (or roots) of teeth 128D, 128E, as shown in FIG. 9B. Teeth 128, 148 are arranged in the first and second jaws 106, 107 such that, when end effector 100 is in a closed configuration, a window 149C having a width $w_c$ and height $h_c$ is formed between the jaws 106, 107 proximal to the last pair of teeth (i.e., teeth 128E, see FIG. 9B) in the jaws. In some embodiments, width $w_c$ may be about 25-30 mils (or preferably about 26.5-28.5 mils), and height $h_c$ may be about 4-8 mils (or preferably about 5-7 mils).

The specific geometric shapes and dimensions of the different teeth described above are merely exemplary. Variations in the size and shape of teeth 128 and 148 are within the scope of this disclosure. However, generally, bigger teeth are provided proximate the distal end 130B (i.e., the front) of the jaws 106, 107 than the proximal end 130A (i.e., the back). For example, in first jaw 106, first and second teeth 128A, 128B positioned proximate distal end 130B are bigger than fourth and fifth teeth 128D, 128E positioned proximate proximal end 130A. Similarly, in second jaw 107, first teeth 148A at distal end 130B are bigger than fourth teeth 148D positioned proximate proximal end 130A. In some embodiments, the configuration of teeth in one or both of the jaws 106, 107 may be such that the size (width and/or height) of the teeth decrease from distal end 130B to proximal end 130A. That is, with reference to FIGS. 10A-10C, a width and/or a height of teeth 128 of first jaw 106 may be such that ($h_1$ and/or $w_1$)>($h_2$ and/or $w_2$)>($h_3$ and/or $w_3$)>($h_4$ and/or $w_4$)>($h_5$ and/or $w_5$). Similarly, with reference to FIGS. 11A-11C, a width and/or a height of teeth 148 in second jaw 107 may be such that ($h_6$ and/or $w_6$)>($h_7$ and/or $w_7$)>($h_8$ and/or $w_8$)>($h_9$ and/or $w_9$). In some embodiments, bigger front teeth may improve anchoring of the jaws into target tissue 50 (see FIG. 1) during tissue acquisition. Better anchoring of the jaws into tissue may increase the depth of the tissue that may be acquired, thereby leading to increased volume of the acquired tissue and improved accuracy of tissue analysis (e.g., histopathology analysis).

An exemplary method of using device 20 will now be described. With reference to FIG. 1, endoscope 4 (or another device having a lumen) is introduced into the body of a patient (e.g., through a body orifice) and positioned such that its distal end 6 is suitably positioned (e.g., in the biliary tract) in the body. Device 20 is then inserted into the body through a working channel of endoscope 4 (e.g., SpyScope DS™) with its end effector 100 in a closed configuration and positioned such that end effector 100 is suitably positioned proximate target tissue 50. As explained previously, in some embodiments, device 20 may be inserted into the body directly or through the lumen of another suitable device. As device 20 is inserted into the body, its flexible coil 28 (see FIG. 2) may flex to navigate through tortuous curves in the body cavity (e.g., the biliary tract includes sections that curve at an acute angle). As device 20 travels through the body cavity, the smaller rigid length (e.g., rigid length of about 3.5 mm in some cases) of end effector 100 (compared to traditional biopsy forceps) enables end effector 100 to pass easily through the acute angle curvatures in the body cavity.

Figure 12A:
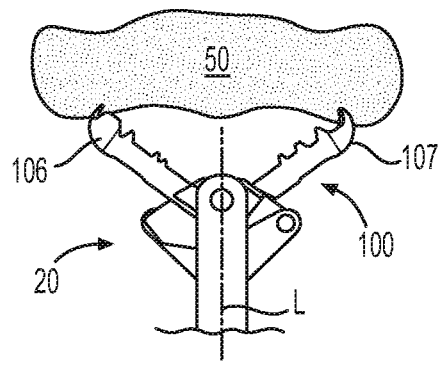
FIGS. 12A-12D illustrate the tissue collection device of FIG. 2 during different stages of an exemplary tissue collection procedure.
Figure 12B:
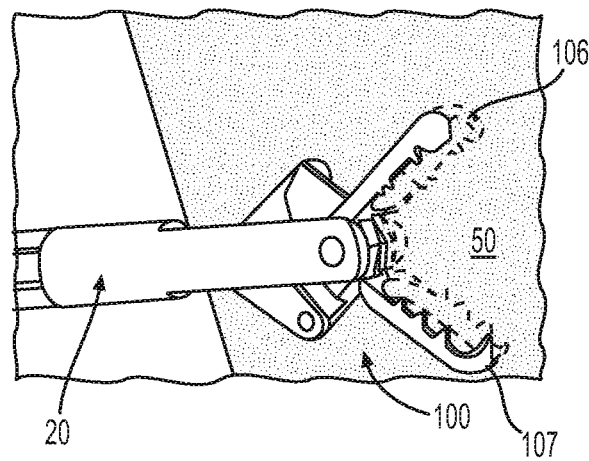

Once end effector 100 is positioned as desired adjacent to the target tissue 50 (see FIG. 1), spool 18 on handle 14 (see FIG. 2) is advanced distally, moving control wire 40 and thus, the control wire 112 attachment distally. With reference to FIG. 3C, the distal movement of control wire attachment 112 pivots the two links 110 about link pins 170 and actuating pins 142, 144, to rotate the first and second jaws 106, 107 about pivot pin 138 and transform end effector 100 to its open tissue-receiving configuration. When end effector 100 is in the open configuration, its open first and second jaws 106, 107 are pushed against target tissue 50. See FIG. 12A. As known to people skilled in the art, end effector 100 may be maneuvered to the target tissue 50 using a viewing system of endoscope 4 or by another suitable method. It should be noted that FIG. 12A illustrates obtaining a perpendicular bite of tissue from target tissue 50 using device 20. As illustrated in FIG. 12A, when obtaining a perpendicular bite, the longitudinal axis L of end effector 100 is oriented generally perpendicular to target tissue 50. Device 20 may also be used to obtain a tangential bite of target tissue 50. See FIG. 12B. When obtaining a tangential bite, the side of the open first and jaws 106, 107 are placed in contact with the tissue wall with a portion of target tissue 50 positioned between the jaws 106, 107.

Figure 12C:
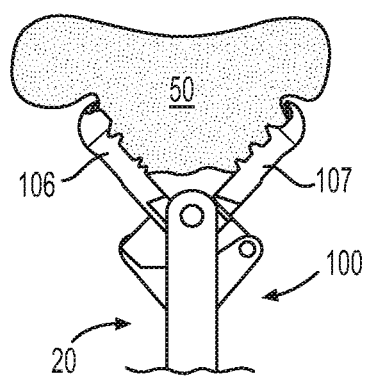
Figure 12D:
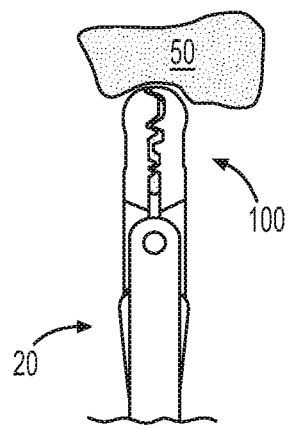

Spool 18 of device 20 is then moved proximally on handle 14 to close the first and second jaws 106, 107. As the jaws 106, 107 rotate towards each other, teeth 128, 148 of the first and second jaw 106, 107 pierce and anchor within the target tissue 50 and cut a portion of the target tissue 50. See FIGS. 12C and 12D. Teeth 128, 148, including the tapered serrations of the jaws, assist in capturing more volume of target tissue 50 and to cleanly cut the tissue. The larger teeth 128, 148 positioned proximate the distal end 130B (see FIGS. 10A, 11A) of the jaws 106, 107 help to increase the depth from which a sample of target tissue 50 may be obtained by end effector 100. When acquiring a tangential bite of tissue (see FIG. 12B), the teeth of the first and second jaws 106, 107 on the side in contact with the target wall, and the front teeth of the first and second jaws 106, 107, anchor and pierce the target tissue 50. The side windows 149A, 149B, and/or 149C (see FIG. 9B) may provide additional space to increase the volume of tissue captured between the jaws and/or reduce tissue crushing. Once tissue has been collected between the first and second jaws 106, 107, device 20 is retracted proximally from the endoscope 4 and the tissue retrieved for diagnosis. If more tissue is desired for the diagnosis, device 20 may be re-inserted through endoscope 4 for further tissue extraction in the same manner.

Figure 13A:
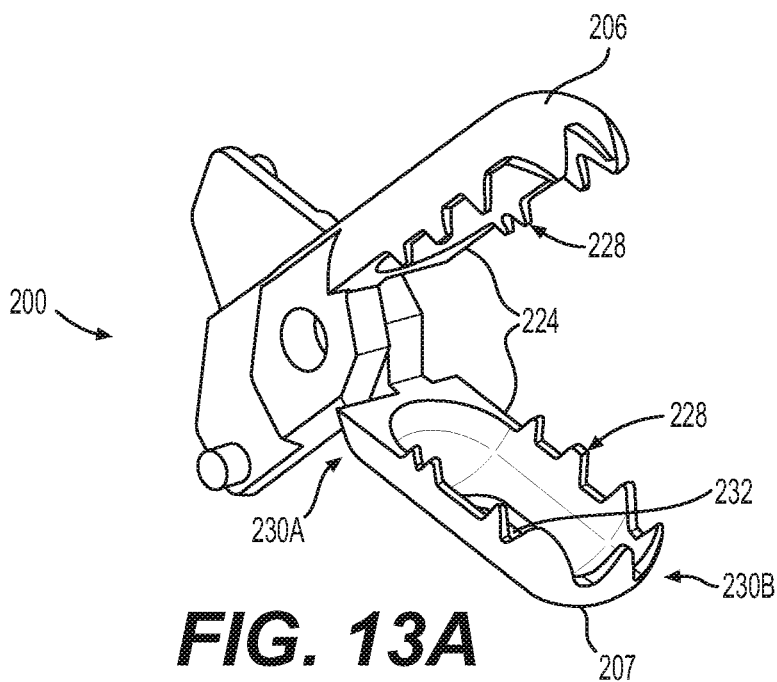
FIGS. 13A-13B illustrate different views of another exemplary end effector of the tissue collection device of FIG. 2.
Figure 13B:
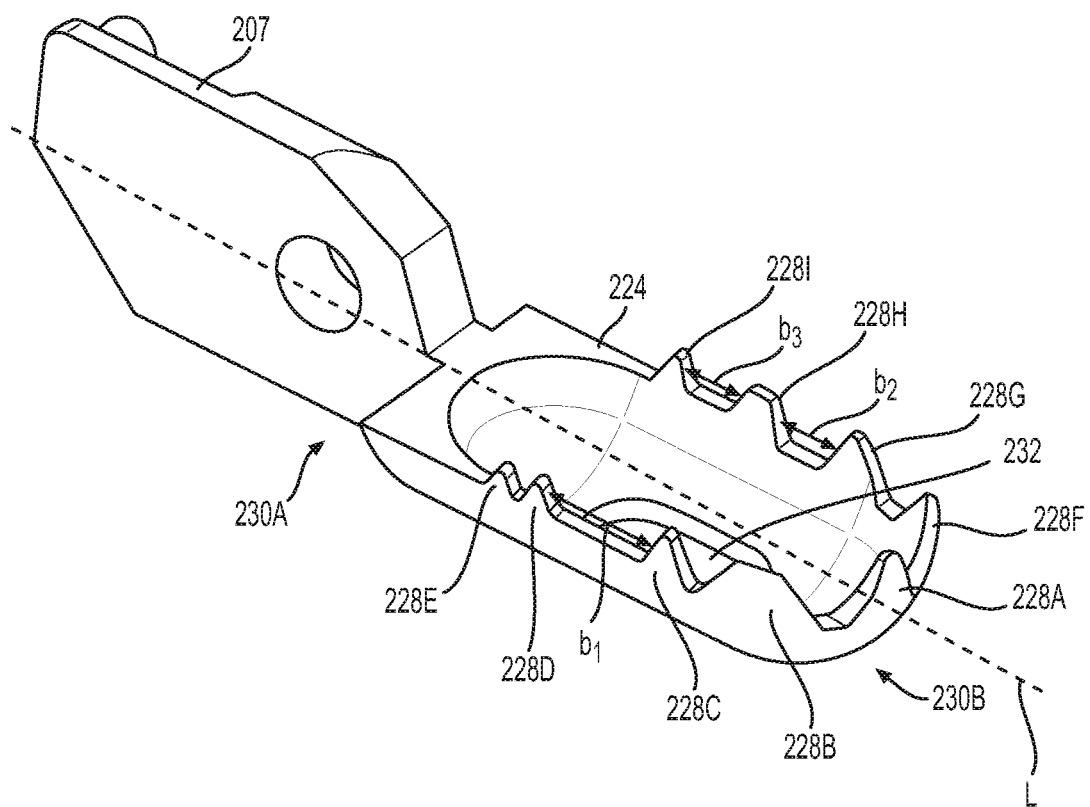

It should be noted that the specific configuration (arrangement and size of teeth, etc.) of end effector 100 described above is only exemplary. In some embodiments, device 20 may include an end effector having a different configuration of teeth. FIG. 13A illustrates a different embodiment of an end effector 200 that may be used in device 20. End effector 200 includes a first jaw 206 and a second jaw 207 rotatably coupled together in the same manner as described with reference to the previously described end effector 100. Each of first jaw 206 and second jaw 207 includes teeth 228 along its tissue cutting edge 224 on the perimeter of the jaw 206, 207. Unlike end effector 100, in end effector 200, both first and second jaws 206, 207 are identical. That is, two identical jaws are used as the first and second jaws 206, 207. Using the same component for both the first and the second jaws 206, 207 decreases the cost of device 20 and assembly complexity. FIG. 13B illustrates a jaw that may be used as each of the first and second jaw of end effector 200. Jaw 207 includes a fenestration hole or aperture 232 (like aperture 132) that extends from its generally concave inner surface to its generally convex outer surface. Although not a requirement, in some embodiments, the minor axis of aperture 232 may be between about 10-20 mils and its major axis may be between 20-40 mils. In some embodiments, the size of aperture 232 may be about 15 mils×30 mils (minor axis× major axis).

As illustrated in FIG. 13B, in jaw 207, teeth 228 are not arranged symmetrically about longitudinal axis L. Since the same component is used as both the first and second jaws 206, 207, the arrangement of the teeth 228 on the left side of the lower jaw 207 is the same as the arrangement of the teeth on the right side of the upper jaw 206. See FIG. 13A. When moving along the left side of tissue cutting edge 224 from distal end 230B to proximal end 230A, teeth 228 of jaw 207 includes a first tooth 228A, a second tooth 228B, a third tooth 228C, a fourth tooth 228D, and a fifth tooth 228E. And, when moving along the right side of tissue cutting edge 224 from distal end 230B to proximal end 230A, jaw 207 includes a sixth tooth 228F, a seventh tooth 228G, an eighth tooth 228H, and a ninth tooth 228I. As illustrated in FIG. 13B, second and eighth teeth 228B, 228H may have a generally trapezoidal shape, and the remaining teeth may have a generally triangular shape. However, in some embodiments, these teeth may have a different shape with pointed, rounded, or flat tips. Teeth 228C and 228D may be separated by a distance $b_1$, teeth 228G and 228H may be separated by a distance $b_2$, and teeth 228H and 228I may be separated by a distance $b_3$. Distance $b_1$ may be about 17-21 mils (preferably about 18-20 mils), and distances $b_2$ and $b_3$ may both be about 5-9 mils (preferably about 6-8 mils). In general, teeth 228 of jaw 207 may have any suitable size. In some embodiments, similar to first jaw 106 of end effector 100, the heights of the teeth 228 of jaw 207 may be such that, a plane passing through the peaks of teeth 228 may make angle $\theta_1$ (see FIG. 10A) with respect to a horizontal plane. Table I below summarizes the approximate heights (base-peak) and widths at base of each of teeth 228 of jaw 207.

TABLE I

Approximate heights and base widths of teeth 228 (of FIG. 13B) in mils (0.001 inches).

| Tooth (see FIG. 13B) | Height (base to peak) in mils | Width at base in mils |
| --- | --- | --- |
| 228A | about 7-11 (or preferably about 8-10) | about 9-13 (or preferably about 10-12) |
| 228B | about 7-12 (or preferably about 8-11) | about 16-20 (or preferably about 17-19) |
| 228C | about 4-8 (or preferably about 5-7) | about 6-10 (or preferably about 6.5-8.5) |
| 228D | about 2-6 (or preferably about 3-5) | about 4-8 (or preferably about 5-7) |
| 228E | about 1-5 (or preferably about 2-4) | about 3-7 (or preferably about 4-6) |
| 228F | about 8-12 (or preferably about 9-11) | about 9-13 (or preferably about 10-12) |
| 228G | about 6-10 (or preferably about 7-9) | about 8-12 (or preferably about 9-11) |
| 228H | about 4-8 (or preferably about 5-7) | about 6-11 (or preferably about 7.5-9.5) |
| 228I | about 2-6 (or preferably about 3-5) | about 3-8 (or preferably about 4.5-6.5) |

Figure 14A:
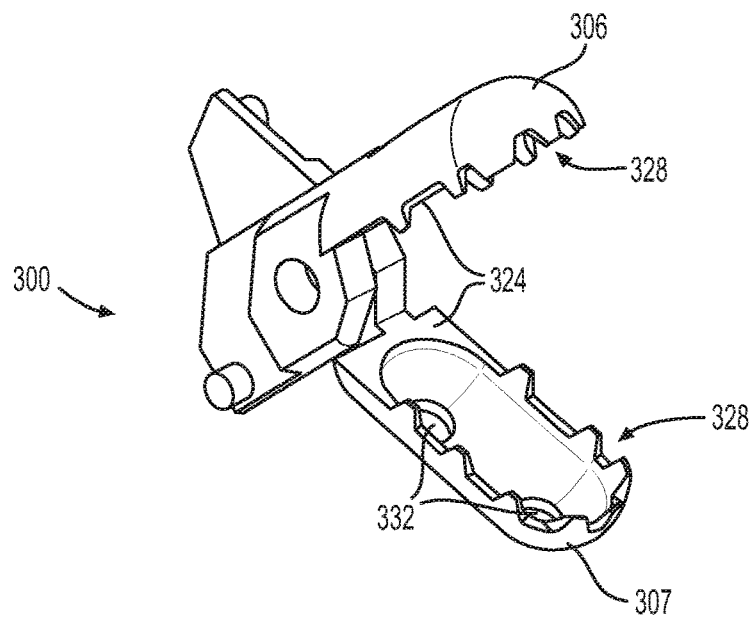
FIGS. 14A-14B illustrate different views of yet another exemplary end effector of the tissue collection device of FIG. 2.
Figure 14B:
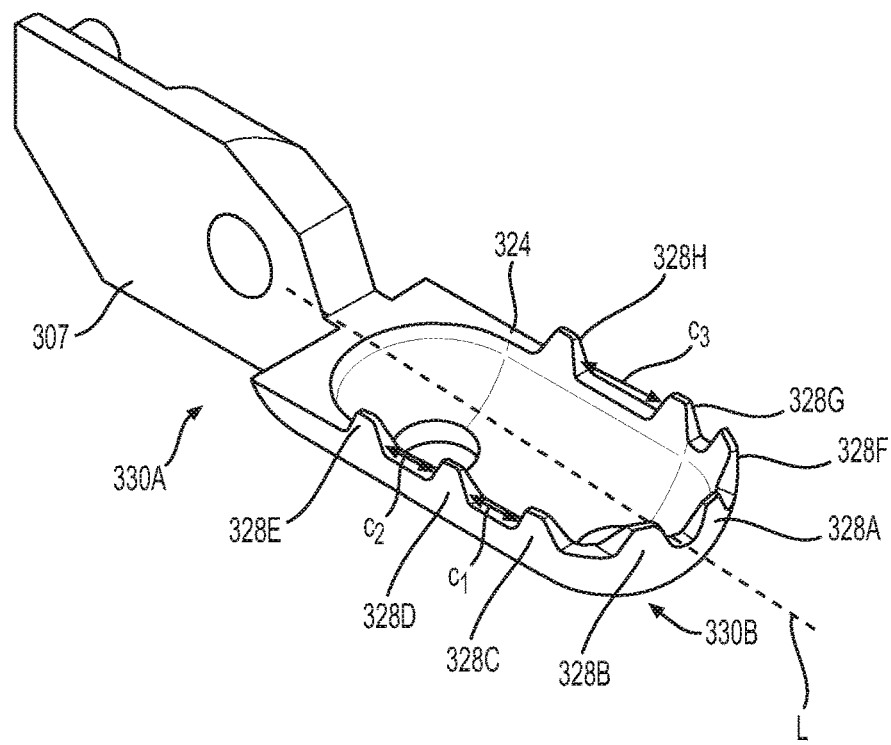

FIG. 14A illustrates another embodiment of an end effector 300 that may be used in device 20. End effector 300 includes a first jaw 306 and a second jaw 307 rotatably coupled together in the same manner as described with reference to the previously described end effector 100. Each of first jaw 306 and second jaw 307 includes teeth 328 along its tissue cutting edge 324 on the perimeter of the jaw. As in end effector 200, in end effector 300, both first and second jaws 306, 307 are identical to decrease assembly complexity and device cost. FIG. 14B illustrates a jaw that may be used as both the first and second jaw 306 and 307 of end effector 300 (referred to as jaw 307 in the description below). Jaw 307 includes two fenestration holes or apertures 332 extending from its generally concave inner surface to its generally convex outer surface. Each of these apertures 332 may be smaller that apertures 132 and 232 of end effectors 100 and 200. Although not a requirement, in some embodiments, the diameter of each aperture 332 may be about 10-15 mils (preferably 12-14 mils). It should be noted that, in some embodiments, jaws (106, 107, 206, 207) of end effectors 100, 200 may also have two fenestration holes or apertures (similar to aperture 332 of end effector 300).

Unlike the previously described embodiments, the teeth 328 in the first and second jaws 306, 307 of end effector 300 may have substantially the same height. Therefore, a plane passing through the tips of teeth 328 may be substantially parallel to the horizontal plane (e.g., a plane parallel to axis L). As illustrated in FIG. 14B, in jaw 307, teeth 328 are not arranged symmetrically about longitudinal axis L. Since the same component is used as both the first and second jaws 306, 307, the arrangement of the teeth 328 on the left side of the lower jaw 307 is the same as the arrangement of the teeth on the right side of the upper jaw 306. See FIG. 14A. When moving along the left side of tissue cutting edge 324 from distal end 330B to proximal end 330A, teeth 328 of jaw 307 includes a first tooth 328A, a second tooth 328B, a third tooth 328C, a fourth tooth 328D, and a fifth tooth 328E. And, when moving along the right side of tissue cutting edge 324 from distal end 330B to proximal end 330A, jaw 307 includes a sixth tooth 328F, a seventh tooth 328G, and an eighth tooth 328H. As illustrated in FIG. 14B, all of these teeth may have a generally trapezoidal shape. Teeth 328C and 328D may be separated by a distance $c_1$, teeth 328D and teeth 328E may be separated by a distance $c_2$, and teeth 328G and 328H may be separated by a distance $c_3$. Distances $c_1$ and $c_2$ may be about 7-12 mils (preferably about 8.5-11 mils), and distance $c_3$ may be about 14-18 mils (preferably about 15-17 mils). As explained previously, the height of all the teeth 328 of jaw 307 may be substantially the same. In some embodiments, the height of teeth 328 may be about 3.5-7.5 mils (preferably about 4.5-6.5 mils). In general, these teeth 328 may have any width. Table II below summarizes the approximate widths of each teeth 328 of jaw 307.

TABLE II

Approximate widths of teeth 328 (of FIG. 14B) in mils (0.001 inches).

| Tooth (see FIG. 14B) | Width at base | Width at peak |
| --- | --- | --- |
| 328A | about 6.5-10.5 (or preferably about 7.5-9.5) | about 1.3-5.3 (or preferably about 2.3-4.3) |
| 328B | about 6.5-10.5 (or preferably about 7.5-9.5) | about 1.3-5.3 (or preferably about 2.3-4.3) |
| 328C | about 6.5-10.5 (or preferably about 7.5-9.5) | about 1.3-5.3 (or preferably about 2.3-4.3) |
| 328D | about 6.5-10.5 (or preferably about 7.5-9.5) | about 1.3-5.3 (or preferably about 2.3-4.3) |
| 328E | about 6.5-10.5 (or preferably about 7.5-9.5) | about 1.3-5.3 (or preferably about 2.3-4.3) |
| 328F | about 9-13 (or preferably about 10-12) | about 4.6-8.6 (or preferably about 5.6-7.6) |
| 328G | about 6.5-10.5 (or preferably about 7.5-9.5) | about 1.3-5.3 (or preferably about 2.3-4.3) |
| 328H | about 6.5-10.5 (or preferably about 7.5-9.5) | about 1.3-5.3 (or preferably about 2.3-4.3) |

Figure 15A:
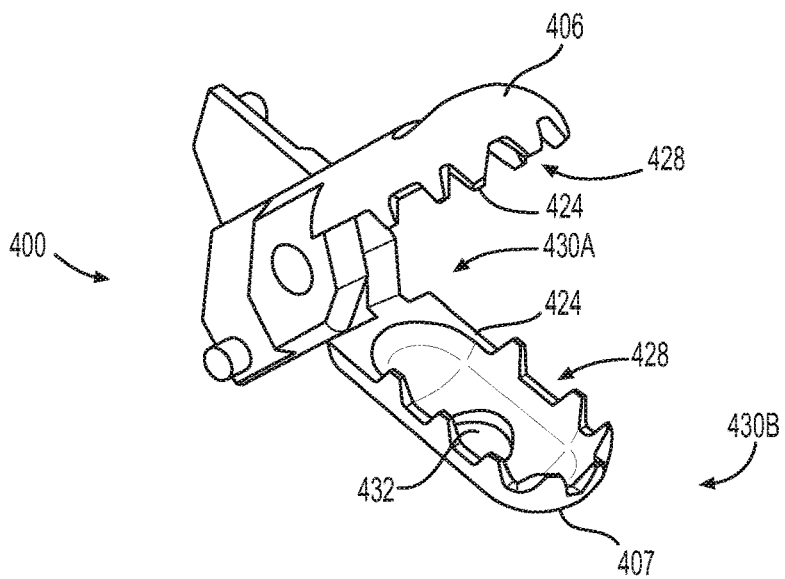
FIGS. 15A-15B illustrate different views of a further exemplary end effector of the tissue collection device of FIG. 2.
Figure 15B:
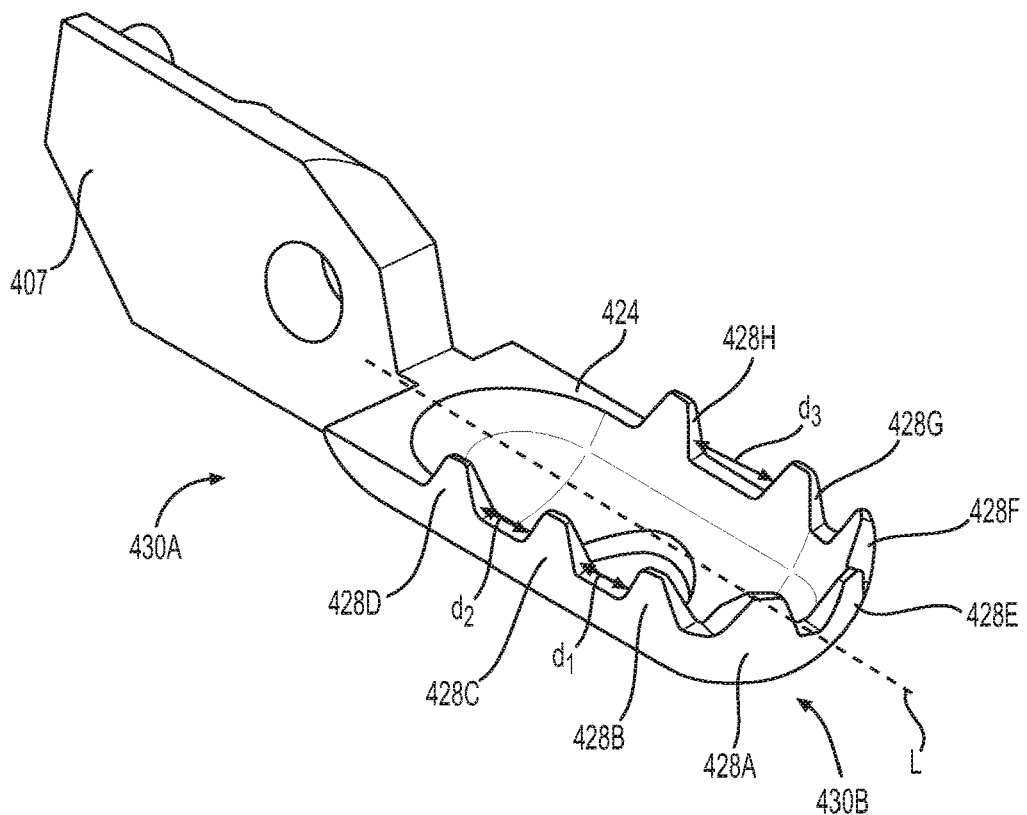

FIG. 15A illustrates another embodiment of end effector 400 that may be used in device 20. End effector 400 includes a first jaw 406 and a second jaw 407 rotatably coupled together in the same manner as described with reference to the previously described end effector 100. Each of first jaw 406 and second jaw 407 includes teeth 428 along its tissue cutting edge 424 on the perimeter of the jaw. As in end effectors 200 and 300, in end effector 400, both first and second jaws 406, 407 are identical to decrease assembly complexity and device cost. FIG. 15B illustrates a jaw that may be used as both the first and second jaw 406 and 407 of end effector 400 (referred to as jaw 407 in the description below). Jaw 407 incudes a single larger fenestration hole or aperture 432 (as compared to aperture 332), extending from its generally concave inner surface to its generally convex outer surface. Although not a requirement, in some embodiments, the diameter of aperture 432 may be about 10-30 mils (preferably 15-25 mils).

As in end effector 300, teeth 428 in first and second jaws 406, 407 of end effector 400 may have substantially the same height. In some embodiments, the height of teeth 428 may be about 5-9 mils (preferably about 6-8 mils). As illustrated in FIG. 15B, in jaw 407, teeth 428 are not arranged symmetrically about longitudinal axis L. Since the same component is used as both the first and second jaws 406, 407, the arrangement of the teeth 428 on the left side of the lower jaw 407 is the same as the arrangement of the teeth on the right side of the upper jaw 406. See FIG. 15A. When moving along the left side of tissue cutting edge 424 from distal end 430B to proximal end 430A, teeth 428 of jaw 407 include a first tooth 428A, a second tooth 428B, a third tooth 428C, and a fourth tooth 428D. And, when moving along the right side of tissue cutting edge 424 from distal end 430B to proximal end 430A, jaw 407 includes a fifth tooth 428E, a sixth tooth 428F, a seventh tooth 428G, and an eighth tooth 428H. As illustrated in FIG. 15B, all of these teeth may have a generally trapezoidal shape. Teeth 428B and 428C may be separated by a distance $d_1$, teeth 428C and teeth 428D may be separated by a distance $d_2$, and teeth 428G and 428H may be separated by a distance $d_3$. Distances $d_1$ and $d_2$ may be about 6-10.5 mils (preferably about 7.5-9.5 mils), and distance $d_3$ may be about 10.5-14.5 mils (preferably about 11.5-13.5 mils). It should be noted, distances $d_1$, $d_2$, $d_3$ (and other similar teeth separation distances ($a_1$-$a_3$, $b_1$-$b_3$, $c_1$-$c_3$, etc.) discussed throughout the specification) are measured at the cutting edge 424 at the base of the teeth. As explained previously, the height of all the teeth 428 of jaw 407 may be substantially the same. In general, these teeth 428 may have any width. Table III below summarizes the approximate widths of each teeth 428 of jaw 407.

TABLE III

Approximate widths of teeth 428 (of FIG. 15B) in mils (0.001 inches).

| Tooth (see FIG. 15B) | Width at base | Width at peak |
|---|---|---|
| 428A | about 7-12 (or preferably about 8.5-10.5) | about 1-5 (or preferably about 2.3-4.3) |
| 428B | about 7-12 (or preferably about 8.5-10.5) | about 1-5 (or preferably about 2.3-4.3) |
| 428C | about 7-12 (or preferably about 8.5-10.5) | about 1-5 (or preferably about 2.3-4.3) |
| 428D | about 7-12 (or preferably about 8.5-10.5) | about 1-5 (or preferably about 2.3-4.3) |
| 428E | about 7-12 (or preferably about 8.5-10.5) | about 1-5 (or preferably about 2.3-4.3) |
| 428F | about 8-12 (or preferably about 9-11) About 10 mils | about 1-5 (or preferably about 2.3-4.3) |
| 428G | about 7-12 (or preferably about 8.5-10.5) | about 1-5 (or preferably about 2.3-4.3) |
| 428H | about 7-12 (or preferably about 8.5-10.5) | about 1-5 (or preferably about 2.3-4.3) |

It should be noted that the teeth profiles, dimensions, and distances between the teeth described with reference to the different embodiments are approximate values. For example, although a tooth is described as being generally trapezoidal or generally triangular, in some embodiments, the same tooth may have a different shape. Any tooth described above may have a rounded, pointed, sharp, curved, or flat tip profile along its width direction (e.g., with reference to tooth 228C of FIG. 13B, in the direction of axis L). Also, the tip of any described tooth may have a rounded, pointed, sharp, curved, or flat tip profile along its thickness direction (e.g., with reference to tooth 228C of FIG. 13B, in a direction transverse to axis L).

It should also be noted that, although a specific configuration of aperture (e.g., aperture 132, 232, 332, 432) is described with reference to each embodiment of device (device 100, 200, 300, 400), in general, any configuration and number of apertures may be provided on one or both jaws in each embodiment of device. For example, in some embodiments, only first jaw 106 (or second jaw 107) of device 100 may include aperture 132, and this aperture may have the configuration of aperture 332 of device 300 (or aperture 432 of device 400). Also in some embodiments of device 100, multiple apertures (of any configuration) may be provided on one or both jaws. In some embodiments, a different number and/or configuration of aperture may be provided in each jaw (e.g., one large aperture in jaw 106 and two smaller apertures in jaw 107, etc.).

In some embodiments, the described teeth profiles, dimensions, and distances on exemplary devices may lead to better tissue retrieval outcomes in terms of tissue size and bite quality. For example, the jaws of described end effectors, which include a combination of bigger and smaller teeth, have better anchoring on tissue due to the layout of the teeth.

It will be appreciated by those skilled in the art that changes may be made to the embodiments described above without departing from the inventive concept thereof. It should further be appreciated that structural features and methods associated with one of the embodiments can be incorporated into other embodiments. It is understood, therefore, that this invention is not limited to the particular embodiment disclosed, but rather modifications are also covered within the scope of the present invention as defined by the appended claims.

We claim:

1. A biopsy forceps device, comprising:
   an end effector including a first jaw opposing a second jaw, wherein the first jaw and the second jaw are coupled together and configured to move from an open configuration to a closed configuration,
   wherein the first jaw includes a first edge and the second jaw includes a second edge, and wherein at least a portion of the first edge contacts at least a portion of the second edge in the closed configuration of the end effector,
   wherein the first jaw includes a first plurality of teeth each having a base and a peak, wherein and the second jaw includes a second plurality of teeth each having a base and a peak, and
   wherein, in the closed configuration of the end effector:
      a gap is formed between (a) a portion of the first edge that extends between the base of a proximalmost tooth of the first plurality of teeth and the base of a second-most proximal tooth of the first plurality of teeth, and (b) a portion of the second edge that extends along the peak of a proximalmost tooth of the second plurality of teeth, a first window is defined between the first edge of the first jaw and the second edge of the second jaw, wherein the first window is proximal to the proximalmost tooth of the first plurality of teeth and the proximalmost tooth of the second plurality of teeth, wherein the first window has a first maximum height, a second window is defined between the first edge of the first jaw and the second edge of the second jaw, wherein the second window is distal to (a) the first window and (b) the proximalmost tooth of the first plurality of teeth and the proximalmost tooth of second plurality of teeth, wherein the second window has a second maximum height, and a third window is defined between the first edge of the first jaw and the second edge of the second jaw, wherein the third window is distal to the first window and the second window, wherein the third window has a third maximum height, wherein the first maximum height is greater than the second maximum height, and wherein the third maximum height is greater than the second maximum height.

2. The device of claim 1, wherein at least one tooth of the first plurality of teeth has a triangular shape, at least another tooth of the first plurality of teeth has a trapezoidal shape, at least one tooth of the second plurality of teeth has a triangular shape, and at least another tooth of the second plurality of teeth has a trapezoidal shape.

3. The device of claim 1, wherein the first plurality of teeth are arranged on the first jaw to be symmetric about a longitudinal axis of the end effector, and the second plurality of teeth are arranged on the second jaw to be symmetric about the longitudinal axis.

4. The device of claim 1, wherein each of the first jaw and the second jaw includes a curved interior surface and a convex outer surface, and wherein the curved interior surface of each of the first jaw and the second jaw together define a tissue receiving space when the end effector is in the closed configuration.

5. The device of claim 1, wherein each of the first jaw and the second jaw extends from a proximal end to a distal end, and wherein (a) one or more teeth of the first plurality of teeth that are positioned at the distal end of the first jaw are bigger than one or more other teeth of the first plurality of teeth that are position at the proximal end of the first jaw, and (b) one or more teeth of the second plurality of teeth that are positioned at the distal end of the second jaw are bigger than other teeth of the second plurality of teeth that are positioned at the proximal end of the second jaw.

6. The device of claim 1, wherein the first plurality of teeth are arranged on the first jaw such that a plane extending along an edge of the peaks of (1) one or more teeth of the first plurality of teeth positioned at a distal end of the first jaw and (2) one or more teeth of the first plurality of teeth positioned at a proximal end of the first jaw is inclined with respect to a horizontal plane by an angle of 2-10 degrees.

7. The device of claim 1, wherein the second plurality of teeth are arranged on the second jaw such that a plane extending along an edge of the peaks of (1) one or more teeth of the second plurality of teeth positioned at a distal end of the second jaw and (2) one or more second teeth positioned at a proximal end of the second jaw is inclined with respect to a horizontal plane by an angle of 1-5 degrees.

8. The device of claim 1, wherein the proximalmost tooth of the first plurality of teeth has a first height relative to the portion of the first edge that extends between the base of the proximalmost tooth and the base of the second-most proximal tooth of the first plurality of teeth, wherein the second-most proximal tooth has a second height relative to the portion of the first edge that extends between the base of the proximalmost tooth and the base of the second-most proximal tooth, and wherein the first height is less than the second height.

9. The device of claim 1, wherein the second jaw includes a fourth tooth, wherein the fourth tooth is a second-most proximal tooth, wherein the fourth tooth comprises a first cutting edge, a second cutting edge, and a third cutting edge, wherein the first cutting edge extends from a first side of the base of the fourth tooth to the second cutting edge, wherein the third cutting edge extends from a second side of the base of the fourth tooth to the second cutting edge, wherein the second cutting edge extends between the first cutting edge and the third cutting edge, and wherein the second cutting edge defines a straight line extending between the first cutting edge and the second cutting edge.

10. The device of claim 1, wherein a maximum height of the second-most proximal tooth of the first plurality of teeth is greater than a maximum height of the proximalmost tooth of the first plurality of teeth.

11. The device of claim 1, wherein, in the closed configuration of the end effector, a first portion of the first edge that extends between (a) the base and (b) the peak of the proximalmost tooth of the first plurality of teeth contacts a first portion of the second edge that extends between (a) the base an (b) the peak of the proximalmost tooth of the second plurality of teeth, and wherein a second portion of the first edge that extends between (a) the base and (b) the peak of the second-most proximal tooth of the first plurality of teeth contacts a second portion of the second edge that extends between (a) the base and (b) the peak of the proximalmost tooth of the second plurality of teeth.

12. The device of claim 1 wherein the first window has a first maximum width, the second window has a second maximum width, and wherein the first maximum width is greater than the second maximum width.

13. A biopsy forceps device, comprising:

an end effector including a longitudinal axis and a first jaw opposing a second jaw, wherein the first jaw and the second jaw are coupled together and configured to move from an open configuration to a closed configuration, wherein the first jaw includes a first edge and the second jaw includes a second edge, wherein at least a portion of the first edge contacts at least a portion of the second edge in the closed configuration of the end effector, wherein the first edge of the first jaw defines a first plurality of teeth, wherein each tooth of the first plurality of teeth has a tip, a proximal base, a proximal side surface extending between the tip and the proximal base, a distal base, and a distal side surface extending between the tip and the distal base;

wherein the second edge of the second jaw includes a second plurality of teeth, wherein each tooth of the second plurality of teeth has a tip, a proximal base, a proximal side surface extending between the tip and the proximal base, a distal base, and a distal side surface extending between the tip and the distal base;

wherein the first edge includes a first tooth, a second tooth, and a third tooth, wherein the first tooth is a proximalmost tooth of the first edge, the second tooth is a second-proximalmost tooth of the first edge, and the third tooth is a third-proximalmost tooth of the first edge;

wherein the second edge includes a fourth tooth, and fifth tooth, wherein the fourth tooth is a proximalmost tooth of the second edge, and the fifth tooth is a second-proximalmost tooth of the second edge, wherein each of the first tooth, the second tooth, and the fourth tooth have a rounded triangular shape;

wherein the fifth tooth has a trapezoid shape; and wherein, in the closed configuration:
- a first window is defined between the first edge of the first jaw and the first edge of the second jaw, wherein at least a portion of a first proximal side surface of the first tooth and at least a portion of a fourth proximal side surface of the fourth tooth form a distal edge of the first window;
- a first distal side surface of a first tooth contacts the fourth proximal side surface of the fourth tooth, and a fourth distal side surface of the fourth tooth contacts a second proximal side surface of the second tooth, such that a gap is formed between a fourth tip of the fourth tooth and a valley of the first edge between a first distal base of the first tooth and a second proximal base of the second tooth,
- a second window is defined between the first edge of the first jaw and the second edge of the second jaw, wherein a second distal side surface of the second tooth forms a proximal edge of the second window, and wherein a fifth proximal side surface of the fifth tooth forms a distal edge of the second window, such that the second window has a parallelogram shape;
- a third window is defined between the first edge of the first jaw and the second edge of the second jaw, wherein a fifth distal side surface of the fifth tooth forms a proximal edge of the third window, and wherein a third proximal side surface of the third tooth forms a distal edge of the third window,
- a fourth distal base of the fourth tooth is closer than a fourth proximal base of the fourth tooth to a longitudinal axis of the end effector, such that the fourth proximal side surface of the fourth tooth is longer than the fourth distal side surface of the fourth tooth;
- a fifth proximal base of the fifth tooth is closer than a fifth distal base of the fifth tooth to a longitudinal axis of the end effector, such that a fifth distal side surface of the fifth tooth is longer than a fifth proximal side surface of the fifth tooth;
- a portion of the first edge extending from a second distal base of the second tooth to a third proximal base of the third tooth forms an upper edge of the second window and the third window, wherein the fifth proximal base and the fifth distal base of the fifth tooth are between the second distal base and the third proximal base, and wherein the upper edge is straight between the second distal base and the third proximal base, and
- a maximum height of the third window is greater than a maximum height of the second window because the fifth proximal base is closer than the fifth distal base to the longitudinal axis.

14. The device of claim 13, wherein the first window has a first maximum width, the second window has a second maximum width, and wherein the first maximum width is greater than the second maximum width.

* * * * *